(12) United States Patent
Fuchiwaki et al.

(10) Patent No.: US 10,886,476 B2
(45) Date of Patent: Jan. 5, 2021

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-Si (KR)

(72) Inventors: Junta Fuchiwaki, Yokohama (JP); Nobutaka Akashi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 266 days.

(21) Appl. No.: 16/164,650

(22) Filed: Oct. 18, 2018

(65) Prior Publication Data

US 2019/0123287 A1  Apr. 25, 2019

(30) Foreign Application Priority Data

Oct. 24, 2017 (KR) .................. 10-2017-0138600

(51) Int. Cl.
| | |
|---|---|
| H01L 51/50 | (2006.01) |
| H01L 51/00 | (2006.01) |
| C07D 471/04 | (2006.01) |
| C09K 11/06 | (2006.01) |
| H01L 51/56 | (2006.01) |

(52) U.S. Cl.
CPC ........ *H01L 51/0072* (2013.01); *C07D 471/04* (2013.01); *C09K 11/06* (2013.01); *C09K 2211/1018* (2013.01); *H01L 51/001* (2013.01); *H01L 51/5012* (2013.01); *H01L 51/5056* (2013.01); *H01L 51/5072* (2013.01);
(Continued)

(58) Field of Classification Search
None
See application file for complete search history.

(56) References Cited

U.S. PATENT DOCUMENTS

| 8,384,068 B2 | 2/2013 | Kahle et al. | |
|---|---|---|---|
| 2014/0091265 A1* | 4/2014 | Stoessel | H05B 33/14 |
| | | | 252/519.21 |
| 2017/0018720 A1 | 1/2017 | Adachi et al. | |

FOREIGN PATENT DOCUMENTS

| JP | 5553758 B2 | 6/2014 |
|---|---|---|
| JP | 5867840 B1 | 1/2016 |

(Continued)

OTHER PUBLICATIONS

Zhang et al., "Theoretical Investigations on Electronic Structures and Photophysical Properties of Novel Bridged Triphenylamine Derivatives," International Journal of Quantum Chemistry. Mar. 2012, vol. 112 Issue 5, p. 1473-1490.

(Continued)

*Primary Examiner* — Gregory D Clark
(74) *Attorney, Agent, or Firm* — Lewis Roca Rothgerber Christie LLP

(57) ABSTRACT

A polycyclic compound may be represented by Formula 1 below. The polycyclic compound may improve the light emitting efficiency of a blue light emitting region, and an organic electroluminescence device including the polycyclic compound may have improved blue light emission, high external quantum efficiency, and long life. The polycyclic compound may be used as a thermally activated delayed fluorescence material, which emits blue light, to improve the blue light emitting efficiency of the organic electroluminescence device.

(Continued)

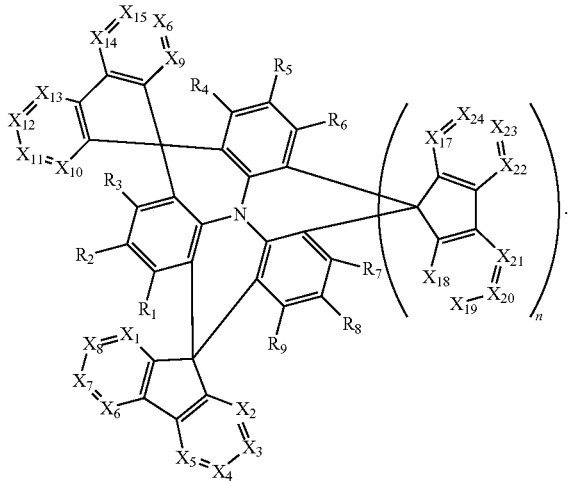

Formula 1

(52) U.S. Cl.
CPC ...... *H01L 51/5088* (2013.01); *H01L 51/5092* (2013.01); *H01L 51/5096* (2013.01); *H01L 51/56* (2013.01); *H01L 2251/558* (2013.01)

(56) References Cited

FOREIGN PATENT DOCUMENTS

| KR | 10-2014-0020208 A | 2/2014 |
| WO | WO 2009/047147 A1 | 4/2009 |
| WO | WO 2012/163471 A1 | 12/2012 |
| WO | WO 2015/136880 A1 | 9/2015 |

OTHER PUBLICATIONS

Ohkuma et al., "Thermally Activated Delayed Fluorescence from a Spiro-diazafluorene Derivative," Chemistry Letters 2014, vol. 43 Issue 7, p. 1017-1019.

21 Claims, 1 Drawing Sheet

* cited by examiner

POLYCYCLIC COMPOUND AND ORGANIC ELECTROLUMINESCENCE DEVICE INCLUDING THE SAME

CROSS-REFERENCE TO RELATED APPLICATION

This patent application claims priority to and the benefit of Korean Patent Application No. 10-2017-0138600, filed on Oct. 24, 2017, the entire content of which is hereby incorporated by reference.

BACKGROUND

Recently, as an image display apparatus, an organic electroluminescence device has been actively developed. The organic electroluminescence device is a self-light emitting display, and is different from a liquid crystal display and the like. i In the organic electroluminescence device, the display of images is performed when holes and electrons injected from the first electrode and the second electrode, respectively, are recombined in a light emitting layer to generate light in a light-emitting material (including an organic compound) that is included in the light emitting layer.

An organic electroluminescence device may be composed of, for example, a first electrode, a hole transport layer disposed (e.g., positioned) on the first electrode, a light emitting layer disposed on the hole transport layer, an electron transport layer disposed on the light emitting layer, and a second electrode disposed on the electron transport layer. Holes are injected from the first electrode, and the injected holes move into the hole transport layer to be injected into the light emitting layer. Meanwhile, electrons injected from the second electrode move into the electron transport layer to be injected into the light emitting layer. The holes and electrons injected into the light emitting layer are then recombined to generate excitons in the light emitting layer. However, the organic electroluminescence device is not limited to the above-described configuration, and various modifications are possible.

There is a demand in the industry for organic electroluminescence devices having a low driving voltage, a high light emitting efficiency, and a long lifetime, and there is continued demand for organic electroluminescence device materials that enable such characteristics to be reliably obtained.

For example, in order to obtain a highly efficient organic electroluminescence device, a phosphorescence technique, using triplet state energy or a delayed fluorescent light emitting technique using triplet-triplet annihilation (TTA), is being developed.

For example, a thermally activated delayed fluorescence (TADF) material is being developed, which may make it possible to achieve an internal quantum efficiency of up to about 100%.

Although large numbers of highly efficient thermally activated delayed fluorescence materials that generate red and green light have been proposed, there are few reports of highly efficient thermally activated delayed fluorescence materials that generate blue light having an emission wavelength of about 480 nm or less.

SUMMARY

One or more aspects of embodiments of the present invention are directed toward a polycyclic compound for a highly efficient organic electroluminescence device.

One or more embodiments of the present invention are directed toward a polycyclic compound for a highly efficient organic electroluminescence device including a polycyclic compound in a light emitting layer.

An embodiment of the present disclosure provides a polycyclic compound represented by Formula 1 below:

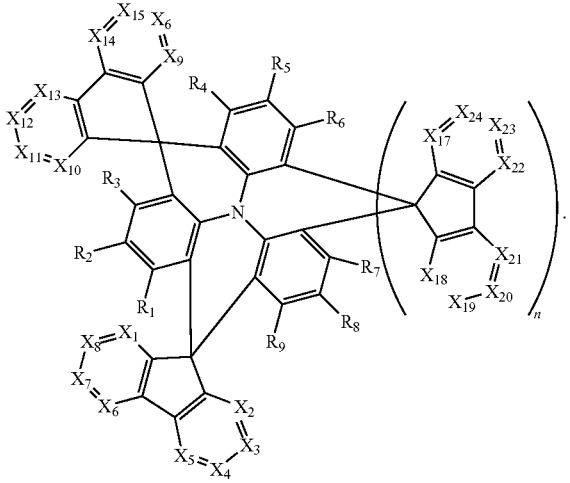

Formula 1

In Formula 1, $X_1$ to $X_{24}$ may be each independently $CR_{10}$ or N.

In Formula 1, at least one of $X_1$ to $X_8$ and at least one of $X_9$ to $X_{16}$ may be N.

In Formula 1, $R_1$ to $R_9$ may be each independently hydrogen, deuterium, a halogen atom, a cyano group, a substituted or unsubstituted silyl group, a substituted or unsubstituted alkyl group having 1 to 12 carbon atoms, a substituted or unsubstituted aryl group having 6 to 30 ring carbon atoms, or a substituted or unsubstituted heteroaryl group having 2 to 30 ring carbon atoms.

In Formula 1, $R_{10}$ may be hydrogen, deuterium, a halogen atom, a cyano group, a substituted or unsubstituted silyl group, a substituted or unsubstituted sulfonyl group, a substituted or unsubstituted alkyl group having 1 to 12 carbon atoms, a substituted or unsubstituted aryl group having 6 to 30 ring carbon atoms, or a substituted or unsubstituted heteroaryl group having 2 to 30 ring carbon atoms.

In Formula 1, n may be 0 or 1.

In an embodiment, Formula 1 may be represented by Formula 1-1 below or Formula 1-2 below:

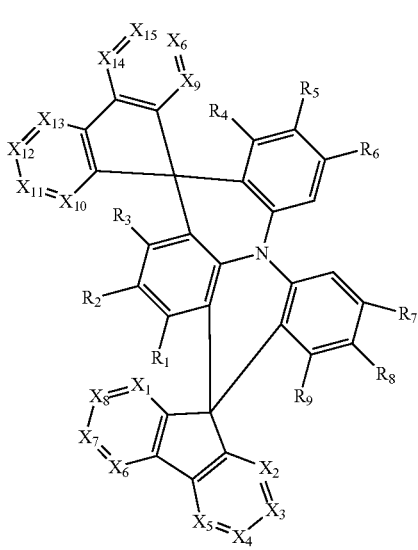

Formula 1-1

Formula 1-2

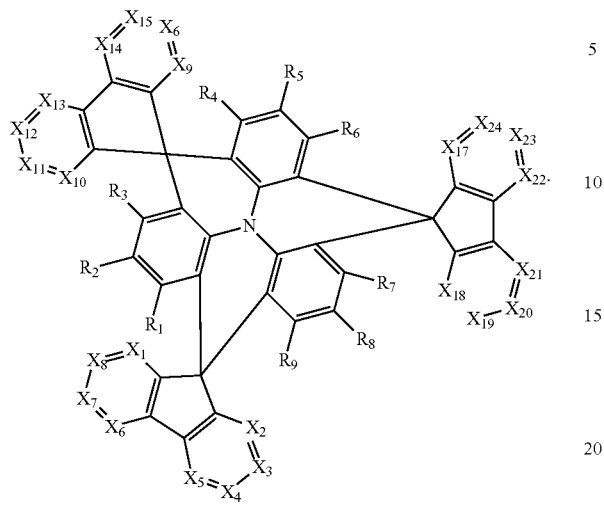

In Formula 1-1 and Formula 1-2, $X_1$ to $X_{24}$, and $R_1$ to $R_{10}$ may be the same as defined in Formula 1.

In an embodiment, at least two of the $X_1$ to $X_8$ and at least two of the $X_9$ to $X_{16}$ may be N.

In an embodiment, when n is 1, at least one of $X_{17}$ to $X_{24}$ may be N, for example, at least two of $X_{17}$ to $X_{24}$ may be N. Further, one of $X_{17}$ or $X_{18}$ may be N, or $X_{17}$ and $X_{18}$ may be both N.

In an embodiment, at least two of $X_1$, $X_2$, $X_9$ or $X_{10}$ may be N, or $X_1$, $X_2$, $X_9$ and $X_{10}$ may be all N.

In an embodiment, $R_1$ to $R_9$ may all be hydrogen atoms, and $R_{10}$ may be an unsubstituted methyl group or a methyl group substituted with a cyano group or a fluorine atom.

In an embodiment, Formula 1 may be one selected from the compounds below (collectively denoted as Compound Group 1):

Compound Group 1

1

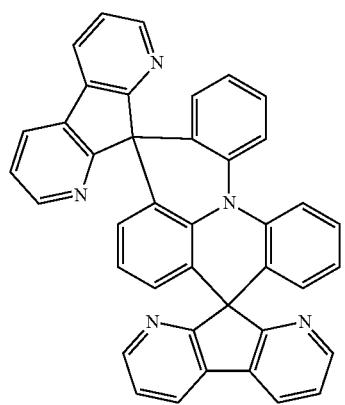

2

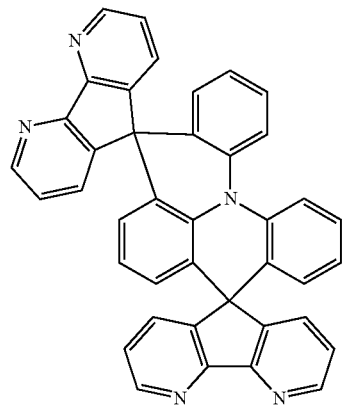

3

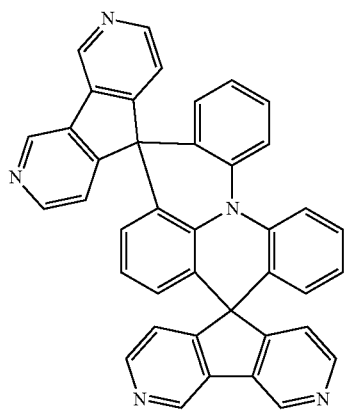

4

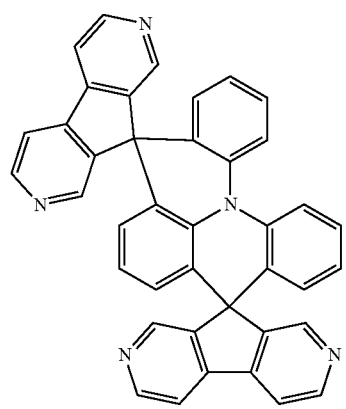

5

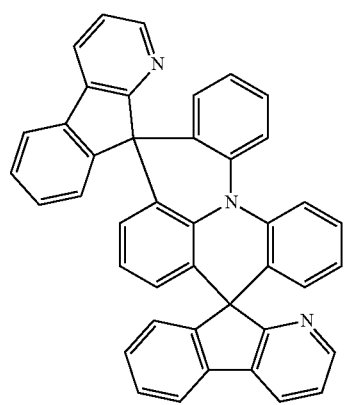

6
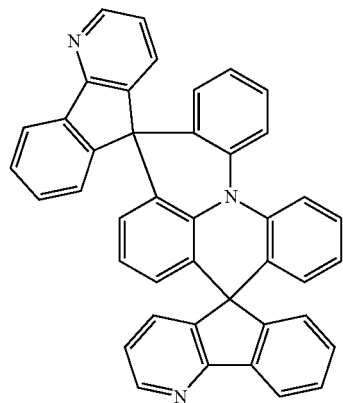
7
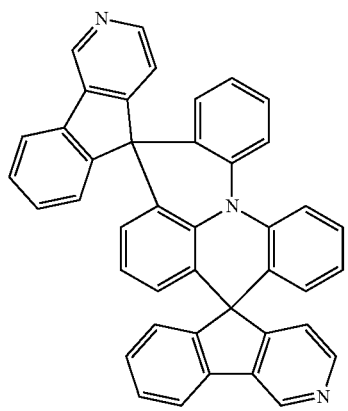
8
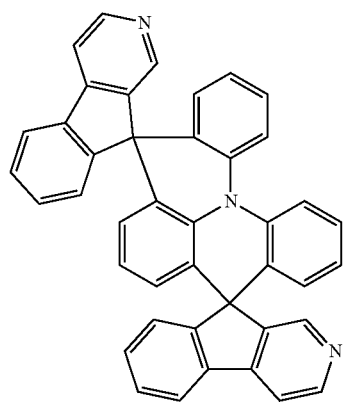
9
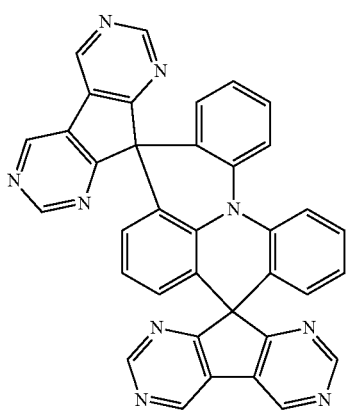
10
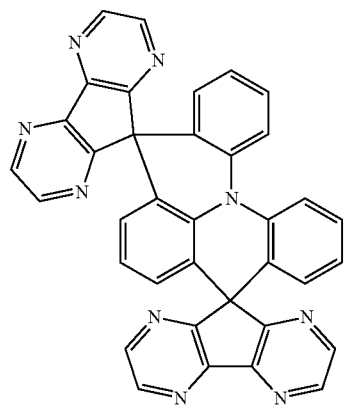
11
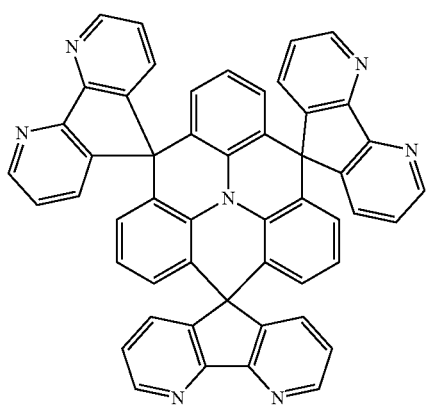
12
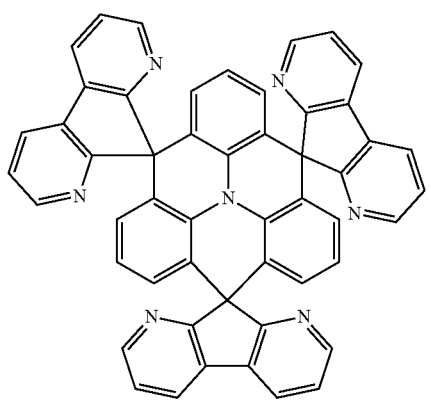
13
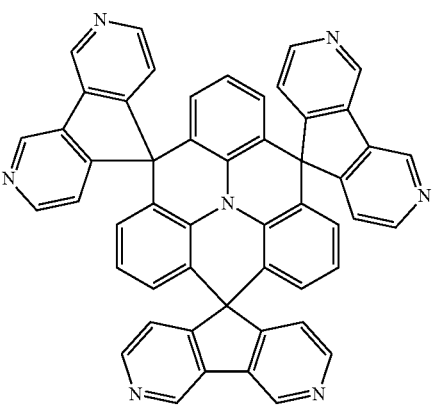

14
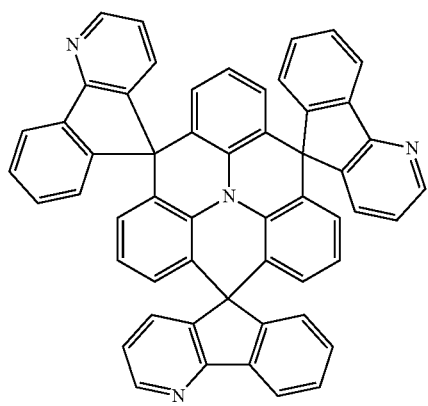
15
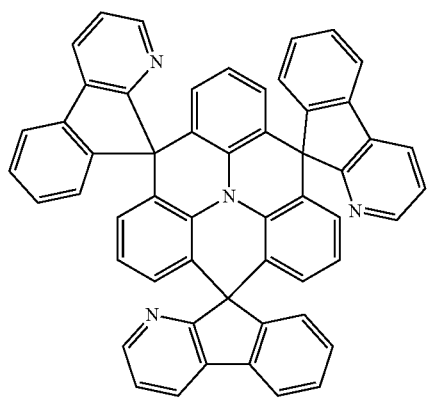
16
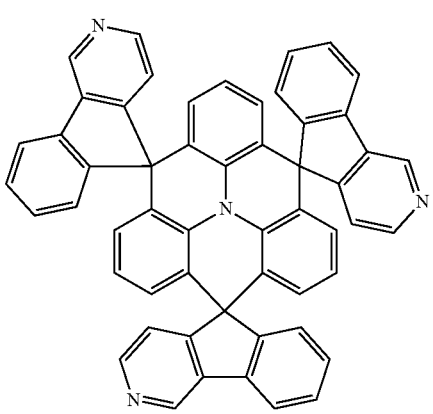
17
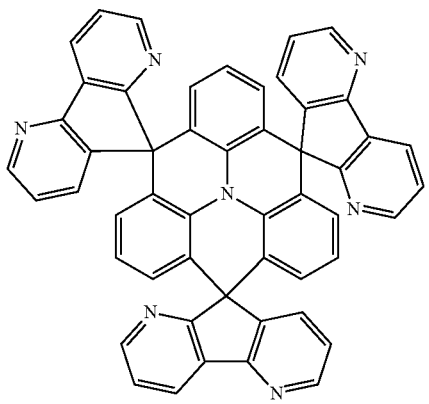
18
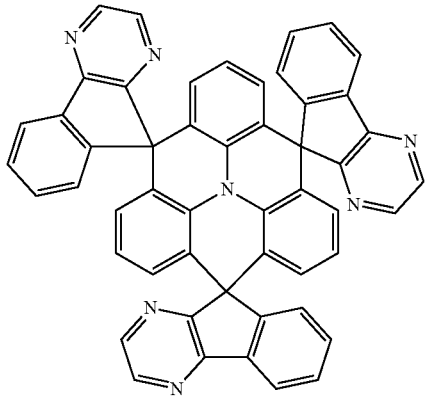
19
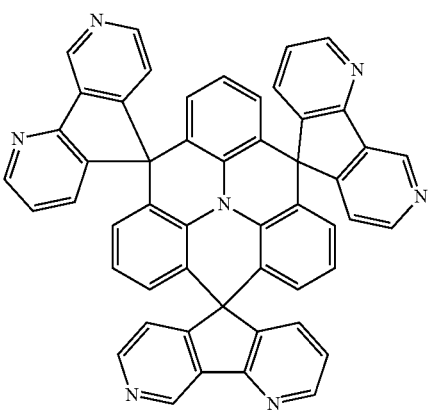

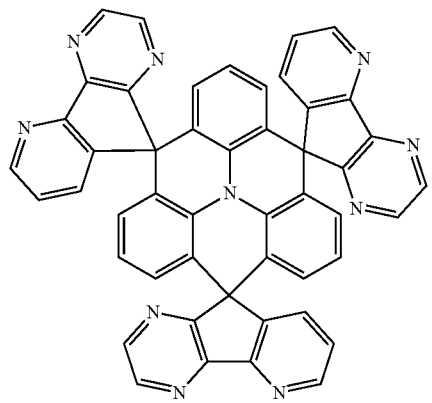

20

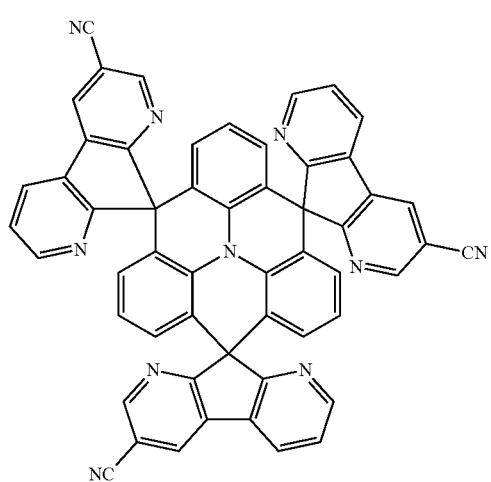

21

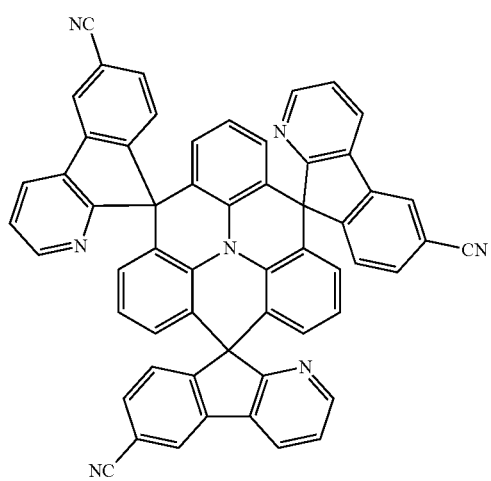

22

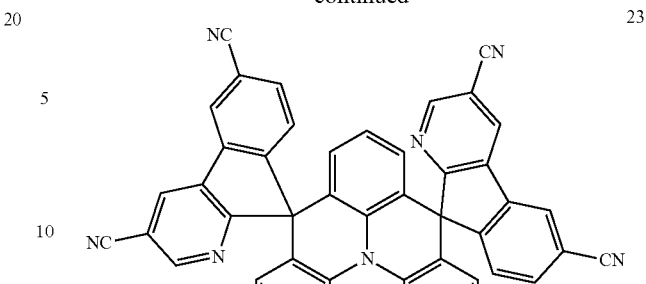

23

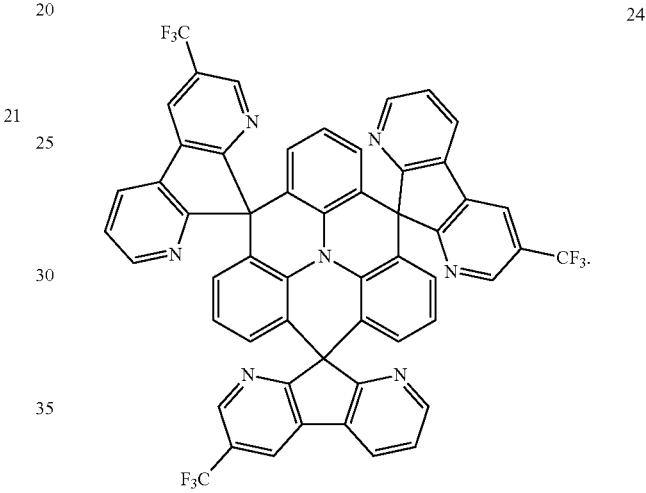

24

In an embodiment of the present disclosure, an organic electroluminescence device may include a first electrode; a hole transport region on the first electrode; a light emitting layer on the hole transport region; an electron transport region on the light emitting layer; and a second electrode on the electron transport region, wherein the light emitting layer may include a polycyclic compound represented by Formula 1 below:

Formula 1

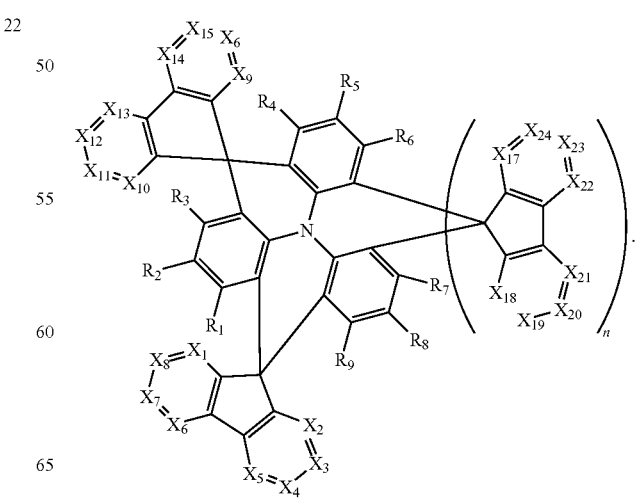

In Formula 1, $X_1$ to $X_{24}$ may be each independently $CR_{10}$ or N.

In Formula 1, at least one of $X_1$ to $X_8$ and at least one of $X_9$ to $X_{16}$ may be N.

In Formula 1, $R_1$ to $R_9$ may be each independently be hydrogen, deuterium, a halogen atom, a cyano group, a substituted or unsubstituted silyl group, a substituted or unsubstituted alkyl group having 1 to 12 carbon atoms, a substituted or unsubstituted aryl group having 6 to 30 ring carbon atoms, or a substituted or unsubstituted heteroaryl group having 2 to 30 ring carbon atoms.

In Formula 1, $R_{10}$ may be hydrogen, deuterium, a halogen atom, a cyano group, a substituted or unsubstituted silyl group, a substituted or unsubstituted sulfonyl group, a substituted or unsubstituted alkyl group having 1 to 12 carbon atoms, a substituted or unsubstituted aryl group having 6 to 30 ring carbon atoms, or a substituted or unsubstituted heteroaryl group having 2 to 30 ring carbon atoms.

In Formula 1, n may be 0 or 1.

In an embodiment, the light emitting layer may emit blue light.

In an embodiment, the light emitting layer may be a fluorescent light emitting layer including a host and a dopant, and the dopant may include the polycyclic compound represented by Formula 1.

In an embodiment, the polycyclic compound represented by Formula 1 may be a thermally activated delayed fluorescence compound, for example, a thermally activated delayed fluorescence dopant.

In an embodiment, the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide of one or more thereof.

In an embodiment, the polycyclic compound represented by Formula 1 may have an absolute value of a difference between a singlet energy level and a triplet energy level of 0.2 eV or less.

In an embodiment, the light emitting layer may include at least one selected from the compounds below (collectively denoted as Compound Group 1):

Compound Group 1

1

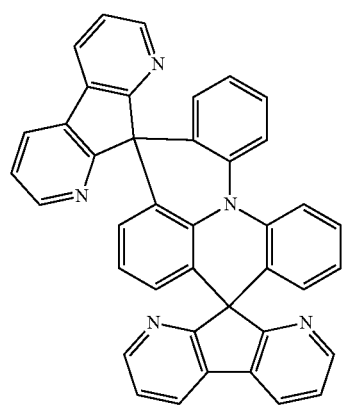

2

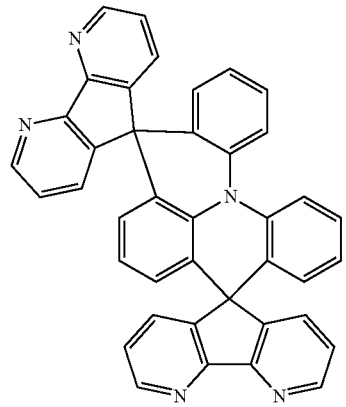

3

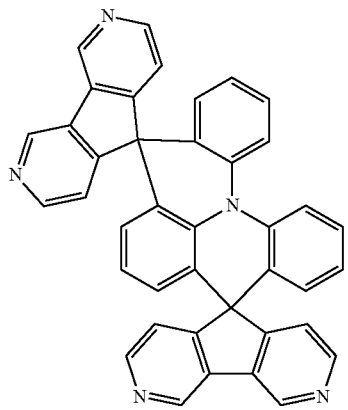

4

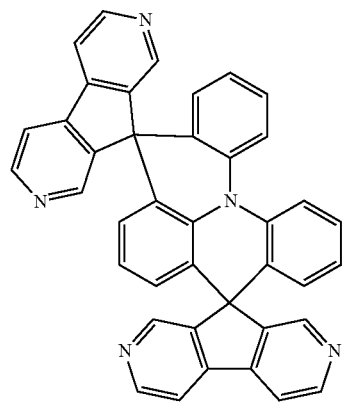

5

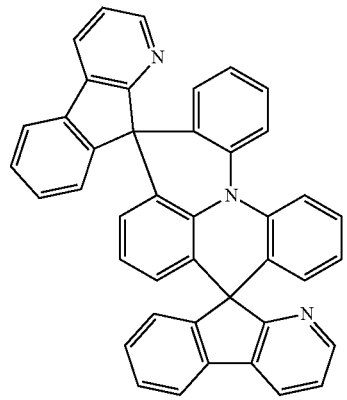

6
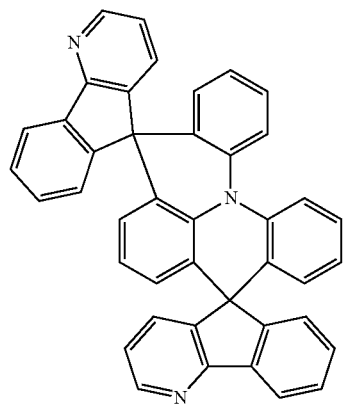
7
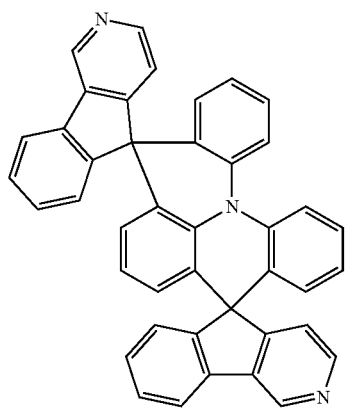
8
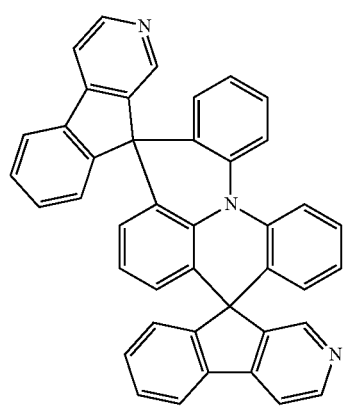
9
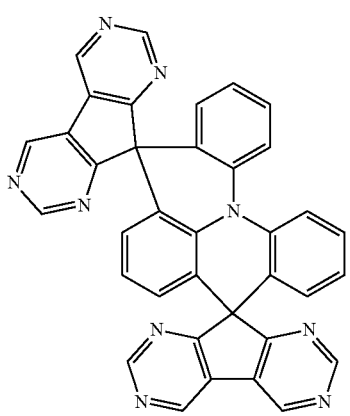
10
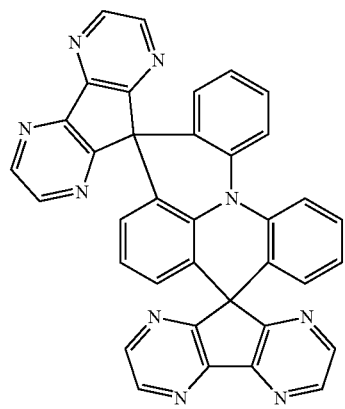
11
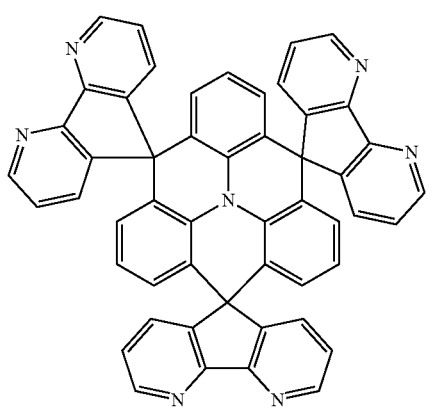
12
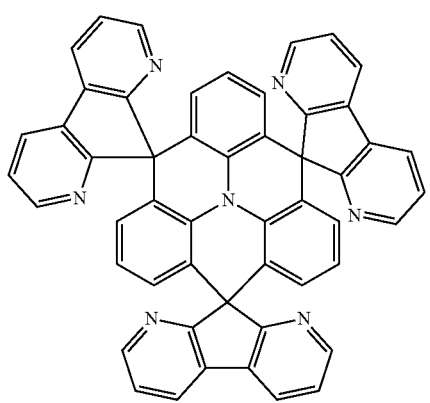
13
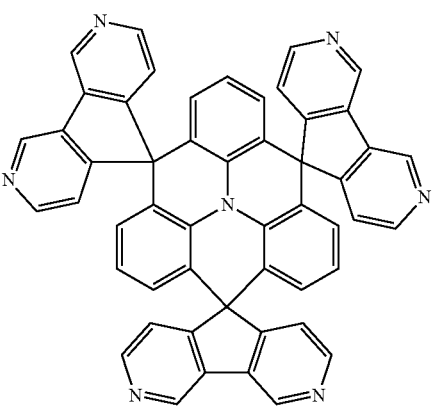

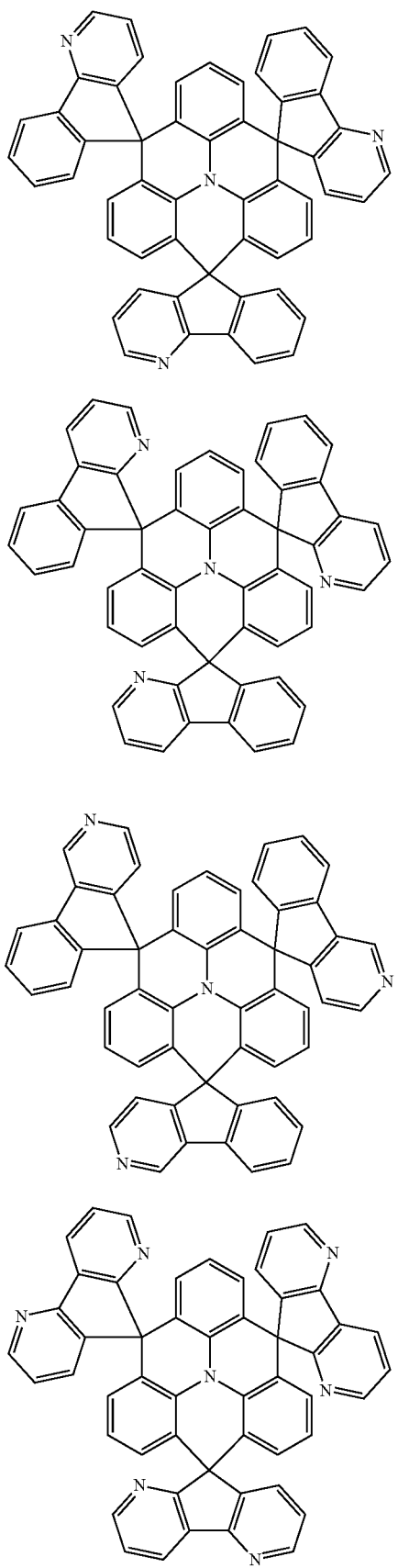
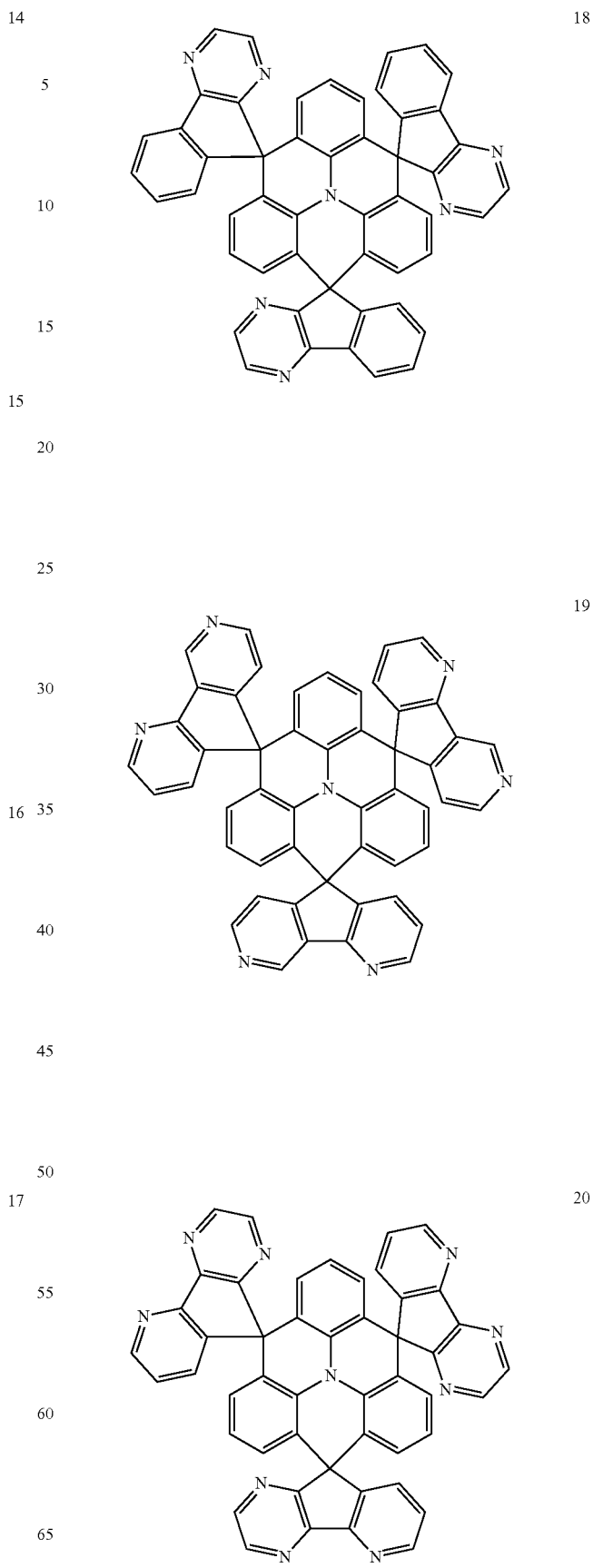

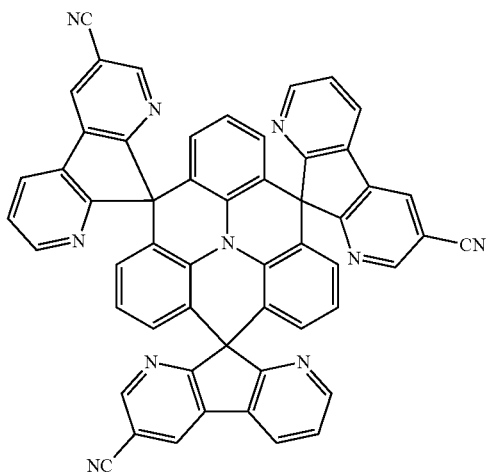

21

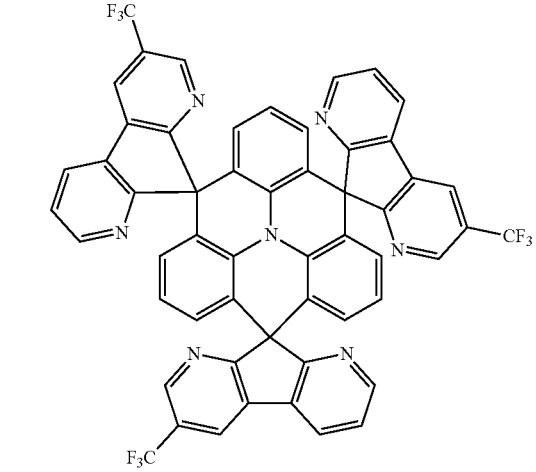

24

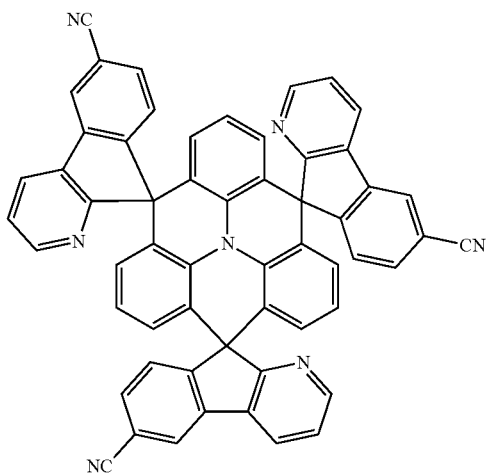

22

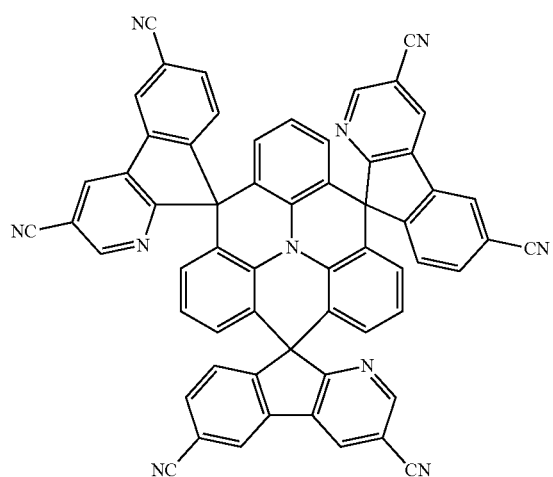

23

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
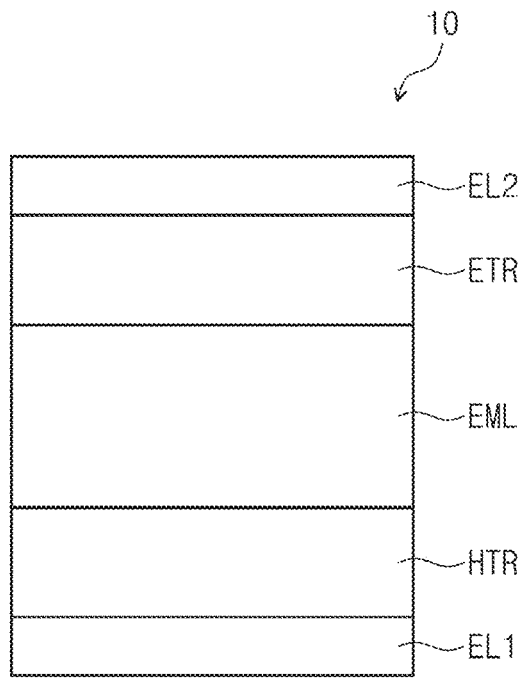
FIG. 1 is a cross-sectional view schematically illustrating an organic electroluminescence device according to an embodiment of the present disclosure.

While the invention is susceptible to various modifications and alternative forms, specific embodiments thereof are shown by way of example in the drawings and are herein described in detail. It should be understood, however, that the invention is not intended to be limited to the particular forms disclosed, but on the contrary, is intended to cover all modifications, equivalents, and alternatives falling within the spirit and scope of the invention.

Like reference numerals have been used for like elements in describing each drawing. In the accompanying drawings, the dimensions of structures are exaggerated for clarity of illustration. Although the terms first, second, etc. may be used herein to describe various elements, these elements should not be limited by these terms. These terms are only used to distinguish one element from another element. For example, without departing from the teachings of the present invention, a first element could be termed a second element, and similarly, a second element could also be termed a first element. The singular forms are intended to include the plural forms as well, unless the context clearly indicates otherwise.

It will be understood that the terms "includes" and/or "including", when used in this specification, indicate the presence of stated features, integers, steps, operations, elements, and/or components, but do not preclude the presence or addition of one or more other features, integers, steps, operations, elements, components, and/or groups thereof. Also, when a portion of a layer, film, region, plate, etc. is referred to as being 'on' another portion, it can be directly on, or intervening portions or elements may also be present.

In the present invention,

denotes a connected position (e.g., a binding site).

In the present specification, the term "substituted or unsubstituted" may refer to a group that is unsubstituted or that is substituted with one or more substituents selected from deuterium, a halogen atom, a nitro group, an amino group, a silyl group, a boron group, a phosphine oxide group, a phosphine sulfide group, an alkyl group, an alkenyl group, an aryl group and a heterocyclic group. Also, each of the exemplified substituents may be substituted or unsubstituted. For example, a biphenyl group may be described as an aryl group, or as a phenyl group substituted with a phenyl group.

In the present specification, the term "combine with a neighboring group to form a ring" may refer to a combination of one substituent group with the neighboring group to form a substituted or unsubstituted hydrocarbon ring, or a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may be monocyclic or polycyclic. Furthermore, the ring formed by the combination of the two neighboring substituent groups may be connected to another ring to form a spiro structure.

In the present specification, "an adjacent group" may refer to a pair of substituent groups where the first substituent is connected to an atom that is directly linked to another atom substituted with the second substituent; a pair of substituent groups connected to the same atom and different from each other; or a pair of substituent groups where the first substituent is most closely positioned sterically to the second substituent. For example, two methyl groups in 1,2-dimethylbenzene may be construed as "adjacent groups", and two ethyl groups in 1,1-diethylcyclopentene may be construed as "an adjacent groups".

In the present specification, examples of the halogen atom include a fluorine atom, a chlorine atom, a bromine atom, and/or an iodine atom.

In the present specification, the alkyl group may be linear, branched, and/or cyclic. The number of carbon atoms in the alkyl group may be 1 or more and 50 or less, 1 or more and 20 or less, 1 or more and 10 or less, or 1 or more and 6 or less. Examples of the alkyl group may include, but are not limited to, a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylhexyl group, a 2-ethylhexyl group, a 4-methyl-2-penthyl group, an n-hexyl group, an 1-methylhexyl group, a 2-ethylhexyl group, a 2-butylhexyl group, a cyclohexyl group, a 4-methylcyclohexyl group, a 4-t-butylcyclohexyl group, an n-heptyl group, an 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-pentyl group, an n-dodecyl group, an ethyldodecyl group, a butyl dodecyl group, a hexyldodecyl group, an octyldodecyl group, an n-tridecyl group, an n-tetradecyl group, an n-pentadecyl group, an n-hexadecyl group, a 2-ethylhexadecyl group, a 2-butyl hexadecyl group, a 2-hexylhexadecyl group, a 2-octylhexadecyl group, an n-heptadecyl group, an n-octadecyl group, an n-nonadecyl, an n-eicosyl group, a 2-ethyl eicosyl group, a 2-butyl eicosyl group, a 2-hexyl eicosyl group, a 2-octyl eicosyl group, an n-hexyl group, an n-docosyl group, an n-tricosyl group, an n-tetracosyl group, a pentacosyl group, an n-hexacosyl group, an n-heptacosyl group, an n-octacosyl group, an n-nonacosyl group, an n-triacontyl group, and the like.

In the present specification, the aryl group may refer to any functional group or substitute derived from an aromatic hydrocarbon ring. The aryl group may be a monocyclic aryl group or polycyclic group. The ring carbon number (e.g., the number of ring-forming carbon atoms) of the aryl group may be 6 or more and 30 or less, 6 or more and 20 or less, or 6 or more and 15 or less. Examples of the aryl group include, but are not limited to, a phenyl group, a naphthyl group, a fluorenyl group, an anthracenyl group, a phenanthryl group, a biphenyl group, a terphenyl group, a quaterphenyl group, a quintaphenyl group, a sextaphenyl group, a triphenylene group, a pyrenyl group, a benzofluoranthenyl group, a chrysenyl group, and the like.

In the present specification, the fluorenyl group may be substituted, and two substituents may bond with each other to form a spiro structure.

In the present specification, the heteroaryl group may include at least one hetero atom selected from O, N, P, Si or S as a ring-forming atom. The ring carbon number of the heteroaryl group may be 2 or more and 30 or less, or 2 or more and 20 or less. The heteroaryl group may be a monocyclic heteroaryl group or a polycyclic heteroaryl. The polycyclic heteroaryl group may have, for example, a bicyclic or tricyclic structure. Examples of the heteroaryl group include a thiophene group, a furan group, a pyrol group, an imidazole group, a thiazole group, an oxazole group, an oxadiazole group, a triazole group, a pyridyl group, a bipyridyl group, a pyrimidyl group, a triazine group, a triazole group, an acridyl groups, a pyridazine group, a pyrazinyl group, a quinolinyl group, a quinazoline group, a quinoxalinyl group, a phenoxazyl group, a phthalazinyl group, a pyridopyrimidinyl group, a pyridopyrazinyl group, a pyrazinopyrazinyl group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophenyl group, a thienothiophenyl group, a benzofuranyl group, a phenanthroline group, a thiazolyl group, an isoxazolyl group, an oxadiazolyl group, a thiadiazolyl group, a benzothiazolyl group, a phenothiazinyl group, a dibenzosilyl group, a dibenzofuranyl group, and the like.

Hereinafter, a polycyclic compound according to an embodiment will be described.

A polycyclic compound of an embodiment is represented by Formula 1 below.

Formula 1

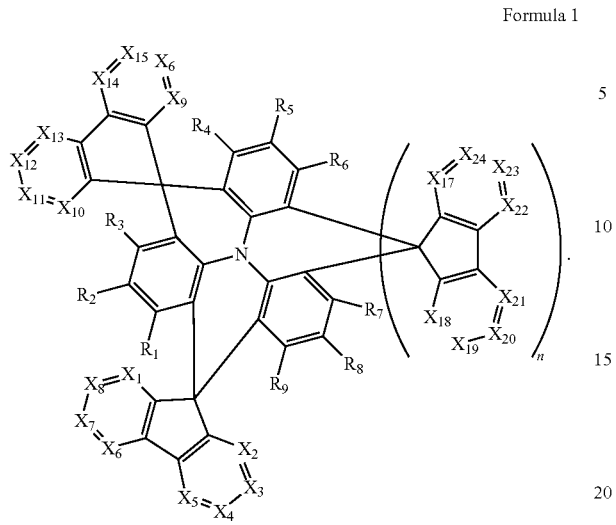

Formula 1-1

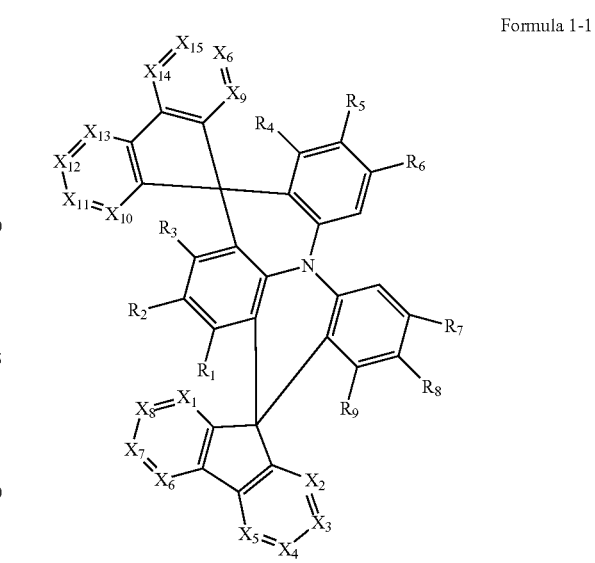

In Formula 1, $X_1$ to $X_{24}$ may be each independently $CR_{10}$ or N. In this case, at least one of $X_1$ to $X_8$ and at least one of $X_9$ to $X_{16}$ is N, while the remaining $X_1$ to $X_8$ and $X_9$ to $X_{16}$ may be $CR_{10}$. For example, at least two of $X_1$ to $X_8$ and at least two of $X_9$ to $X_{16}$ is N, and the remaining $X_1$ to $X_8$ and $X_9$ to $X_{16}$ may be $CR_{10}$. In one or more embodiments, at least two of $X_1$, $X_2$, $X_9$ or $X_{10}$ may be N, for example, $X_1$, $X_2$, $X_9$ and $X_{10}$ may be all N.

$R_1$ to $R_9$ may be each independently hydrogen, deuterium, a halogen atom, a cyano group, a substituted or unsubstituted silyl group, a substituted or unsubstituted alkyl group having 1 or more and 12 or less carbon atoms, a substituted or unsubstituted aryl group having 6 or more and 30 or less ring carbon atoms; or a substituted or unsubstituted heteroaryl group having 2 or more and 30 or less ring carbon atoms. In one or more embodiments, $R_1$ to $R_9$ may be all hydrogen atoms.

In Formula 1, $R_{10}$ may be hydrogen, deuterium, a halogen atom, a silyl group, a substituted or unsubstituted silyl group, a substituted or unsubstituted sulfonyl group, a substituted or unsubstituted alkyl group having 1 or more and 12 or less carbon atoms, a substituted or unsubstituted aryl group having 6 or more and 30 or less ring carbon atoms, or a substituted or unsubstituted heteroaryl group having 2 or more and 30 or less ring carbon atoms. For example, $R_{10}$ may be an unsubstituted methyl group or a methyl group substituted with a cyano group or fluorine atom.

n may be 0 or 1. When n is 1, at least one of $X_{17}$ to $X_{24}$ may be N, and in some embodiments, at least two of the $X_{17}$ to $X_{24}$ may be N. For example, at least one of $X_{17}$ or $X_{18}$ may be N, or $X_{17}$ and $X_{18}$ may be both N.

The polycyclic compound of an embodiment of the present disclosure may be a material for an organic electroluminescence device in which an absolute value of a difference between a singlet energy level and a triplet energy level is 0.2 eV.

In one or more embodiments, the polycyclic compound of an embodiment may be a thermally activated delayed fluorescence (TADF) material. For example, the polycyclic compound of an embodiment may be a thermally activated delayed blue fluorescence dopant, which emits blue light.

The polycyclic compound represented by Formula 1 may be represented by Formula 1-1 or Formula 1-2.

Formula 1-2

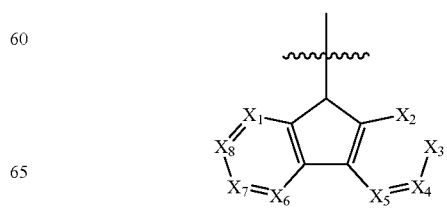

Formula 1-1 represents a case where n in Formula 1 is 0. In Formula 1-1, at least two of $X_1$ to $X_8$ and at least two of $X_9$ to $X_{16}$ may be N. For example, $X_1$ and $X_2$ from among $X_1$ to $X_8$ may each be N, and $X_9$ and $X_{10}$ from among $X_9$ to $X_{16}$ may each be N. It is preferable that in the two azafluorene moieties of Formula 1, the positions of those $X_1$ to $X_8$ that are represented by N correspond (e.g., are the same) as the positions of those $X_9$ to $X_{16}$ that are represented by N, in order to form a symmetry. That is, it is preferable that the positions represented by N in a portion and those in a

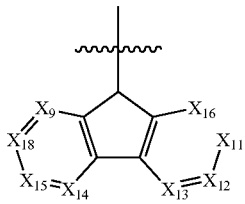

portion are the same as each other, for purposes of forming a symmetric structure. In some embodiments, at least two of $X_1$, $X_2$, $X_9$ or $X_{10}$ may be N, for example, $X_1$, $X_2$, $X_9$ and $X_{10}$ may be all N.

Formula 1-2 represents a case in which n is 1 in Formula 1. In this case, at least one of $X_{17}$ to $X_{24}$ may be N, for example, at least two of $X_{17}$ to $X_{24}$ may be N. For example, when at least two of $X_1$ to $X_8$, at least two of $X_9$ to $X_{19}$ and at least two of $X_{17}$ to $X_{24}$ are N, the positions of each N are preferably symmetric with respect to each other. In some embodiments, at least one of $X_{17}$ or $X_{18}$ may be N.

In one or more embodiments, $R_1$ to $R_9$ may be hydrogen atoms, $R_{10}$ may be an unsubstituted methyl group or a methyl group substituted with a cyano group or a fluorine atom.

In Formula 1-1 and Formula 1-2, $X_1$ to $X_{24}$, and $R_1$ to $R_{10}$ may be respectively defined as in Formula 1.

The polycyclic compound represented by Formula 1 may be any one selected from the compounds below (collectively denoted as Compound Group 1). However, the embodiment is not limited thereto.

Compound Group 1

1
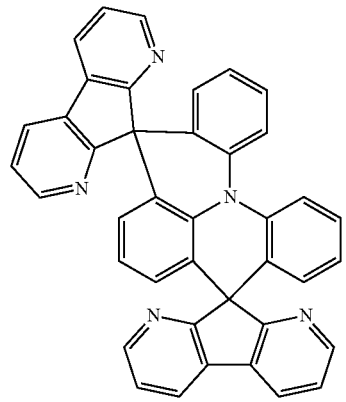

2
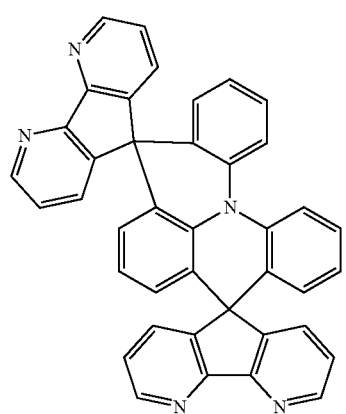

3
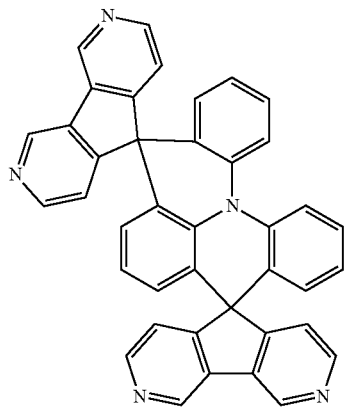

4
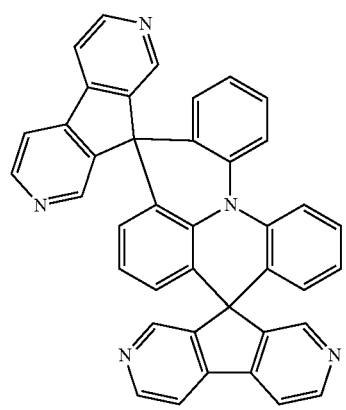

5
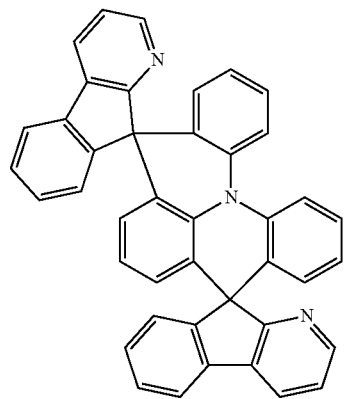

6
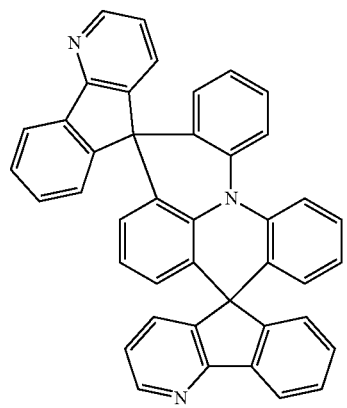

-continued
7
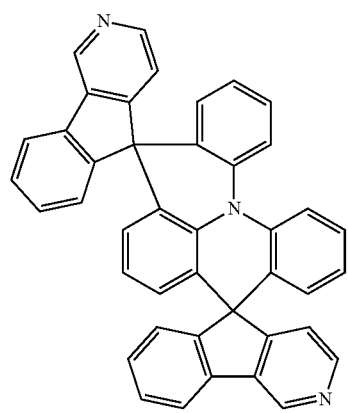
8
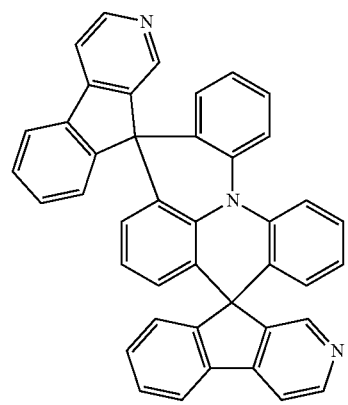
9
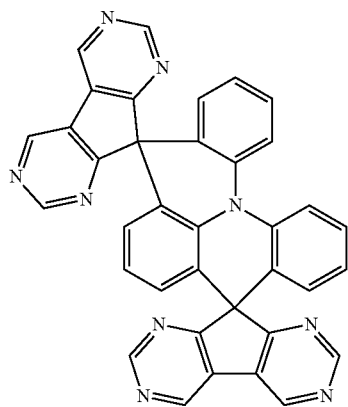
10
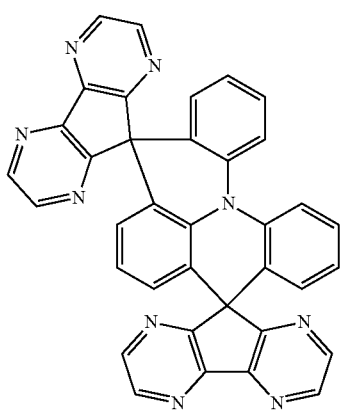
-continued
11
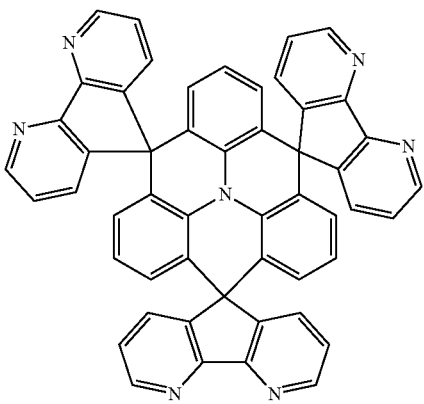
12
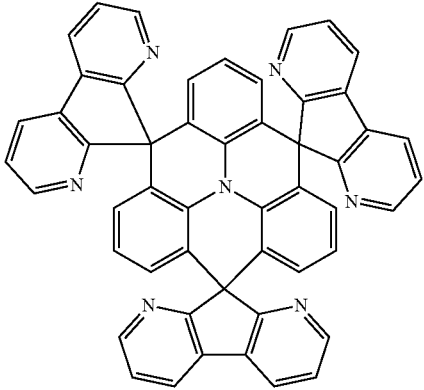
13
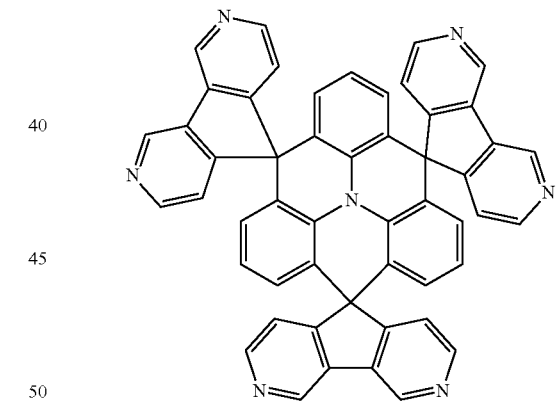
14
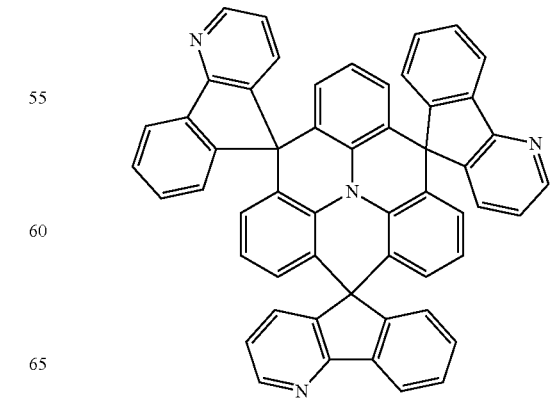

27
-continued
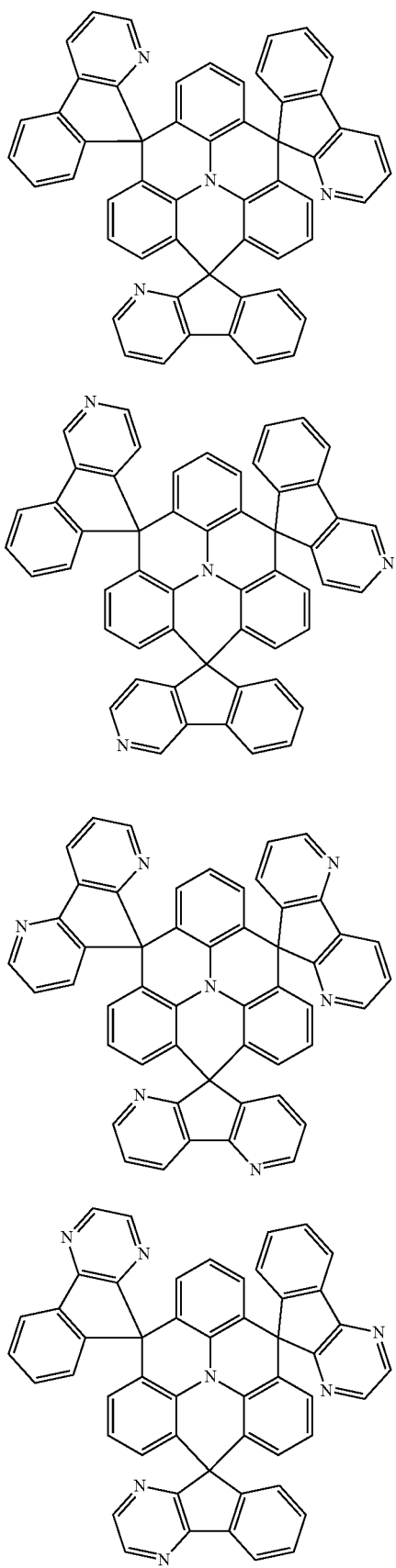
28
-continued
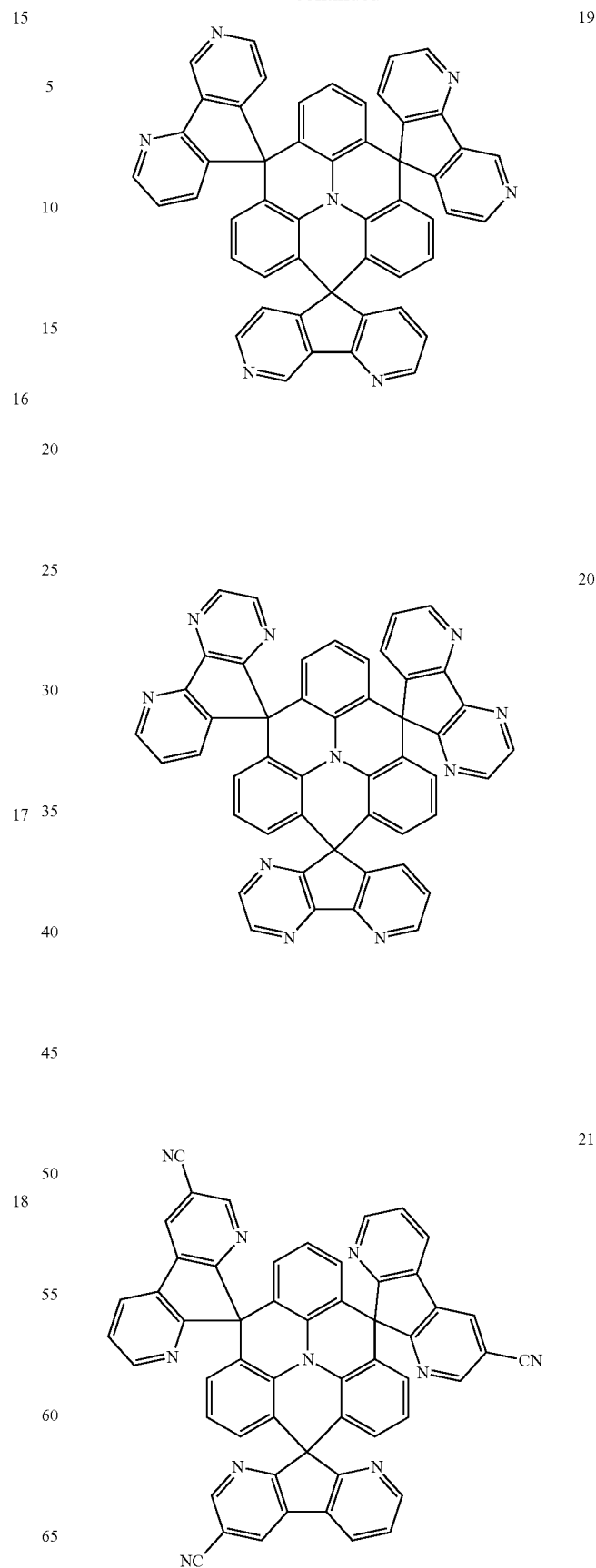

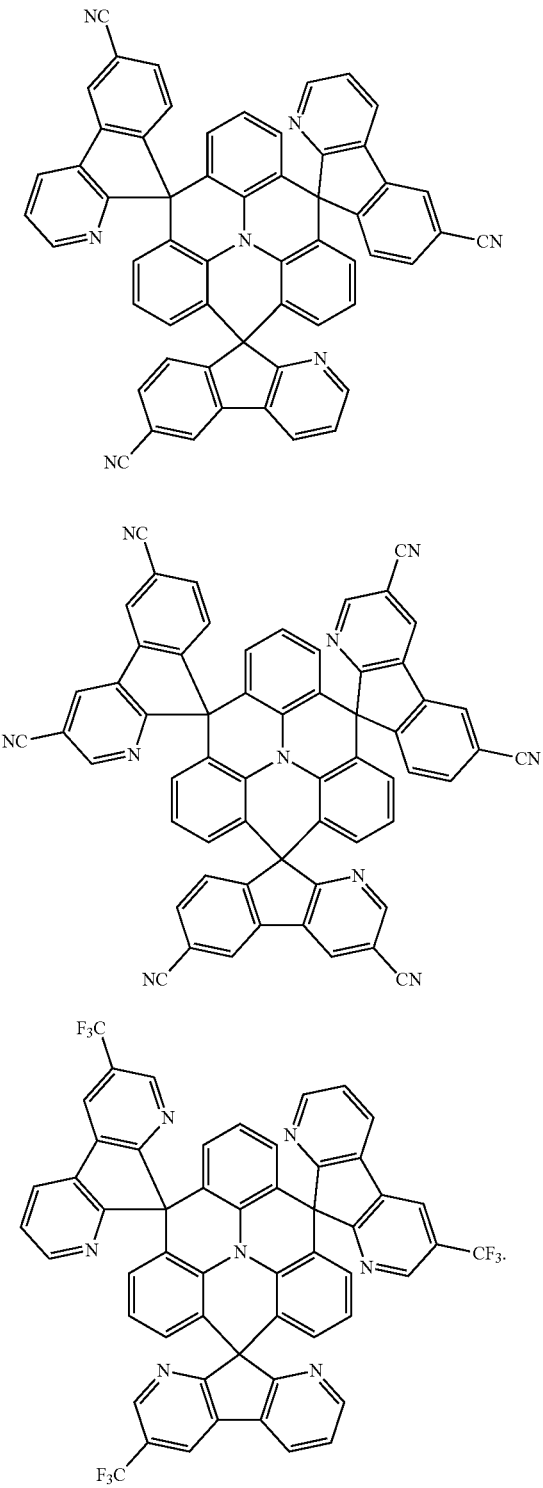

The polycyclic compound of an embodiment described above may be used as a material for an organic electroluminescence device, and may enable the light emitting efficiency of the organic electroluminescence device to be improved. The polycyclic compound of an embodiment may be used as a thermally activated delayed fluorescence material, which emits blue light. The polycyclic compound of an embodiment may be used for an organic electrolumines- cence device to facilitate the emission of a deep blue color, and may exhibit high light emitting efficiency in a blue light emitting region.

Hereinafter, an organic electroluminescence device according to an embodiment of the present disclosure will be described in more detail. However, duplicative descriptions of elements and features already described above will not be provided, as descriptions of these elements and features are the same as those provided above.

Figure 2:
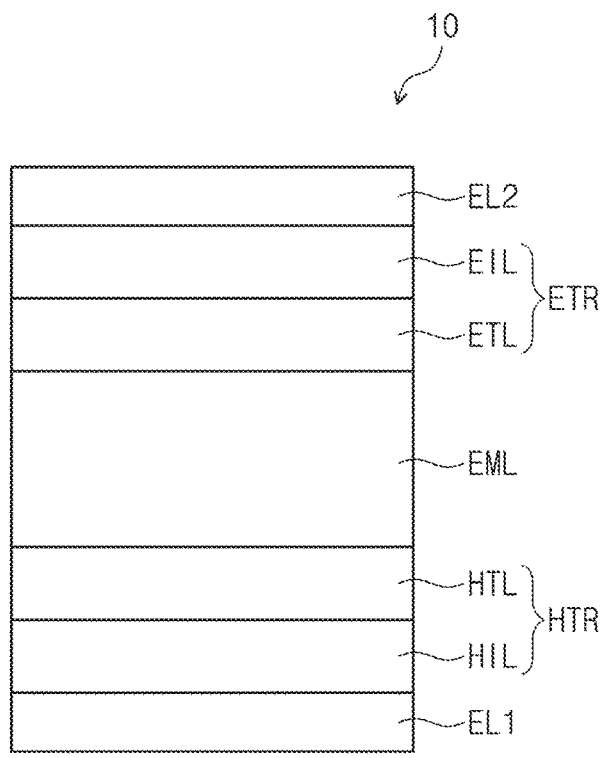
FIG. 2 is a cross-sectional view schematically illustrating an organic electroluminescence device according to an embodiment of the present disclosure.

FIG. 1 and FIG. 2 are cross-sectional views schematically illustrating organic electroluminescence devices according to an embodiment of the present disclosure.

Referring to FIG. 1 and FIG. 2, an organic electroluminescence device according to an embodiment may include a first electrode EL1, a hole transport region HTR, a light emitting layer EML, an electron transport region ETR, and a second electrode EL2, which are sequentially stacked. As illustrated in FIG. 2, the hole transport region HTR may include a hole injection layer HIL and a hole transport layer HTL, and the electron transport region ETR may include an electron injection layer EIL and an electron transport layer ETL.

The first electrode EL1 and the second electrode EL2 may be disposed (e.g., positioned) to face each other, and a plurality of organic layers may be disposed between the first electrode EL1 and the second electrode EL2. The plurality of organic layers may include the hole transport region HTR, the light emitting layer EML, and the electron transport region ETR.

The organic electroluminescence device 10 of an embodiment may include the polycyclic compound of an embodiment in the light emitting layer EML.

In the following description of an organic electroluminescence device 10, a case in which the light emitting layer includes the polycyclic compound of an embodiment will be described in more detail. However, embodiments of the present disclosure are not limited thereto, and the polycyclic compound of an embodiment may be included in at least one layer of a plurality of organic layers disposed between the first electrode EL1 and the second electrode EL2. For example, the polycyclic compound according to an embodiment of the present disclosure may be included in the hole transport region HTR.

The first electrode EL1 has conductivity. The first electrode EL1 may be formed of a metal alloy or any suitable conductive compound. The first electrode EL1 may be an anode.

The first electrode EL1 may be a transmissive electrode, a semi-transmissive electrode, or a reflective electrode. When the first electrode EL1 is a transmissive electrode, the first electrode EL1 may be formed of a transparent metal oxide such as an indium tin oxide (ITO), an indium zinc oxide (IZO), a zinc oxide (ZnO), an indium tin oxide (ITZO), and/or the like. When the first electrode EL1 is a semi-transmissive electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, or a compound or mixture thereof (e.g., a mixture of Ag and Mg). In some embodiments, the first electrode EL1 may have a structure of multiple layers, which may include a reflective film and/or a semi-transmissive film formed of any of the above-exemplified materials and a transparent conductive film formed of the indium tin oxide (ITO), the indium zinc oxide (IZO), the zinc oxide (ZnO), the indium tin oxide (ITZO) and/or the like.

The hole transport region HTR is provided on the first electrode EL1. The hole transport region HTR may include at least one of a hole injection layer HIL, a hole transport layer HTL, a hole buffer layer or an electron blocking layer.

The thickness of the hole transport region HTR may be, for example, about 1000 Å to about 1500 Å.

The hole transport region HTR may have a multilayered structure having a single layer composed of a single material, a single layer composed of a plurality of different materials, or multiple layers composed of a plurality of different materials.

For example, the hole transport region HTR may have a single-layered structure having a hole injection layer HIL or a hole transport layer HTL, or may have a single-layered structure composed of a hole injection material and a hole transporting material. In some embodiments, the hole transport region HTR may have a single-layered structure composed of a plurality of different materials, or may have a structure of the hole injection layer HIL/the hole transport layer HTL, the hole injection layer HIL/the hole transport layer HTL/the hole buffer layer, the hole injection layer HIL/the hole buffer layer, the hole transport layer HTL/the hole buffer layer, or the hole injection layer HIL/the hole transport layer HTL/the electron blocking layer, which are sequentially stacked from the first electrode EL1. However, embodiments of the present disclosure are not limited thereto.

The hole transport region HTR may be formed by using one or more suitable methods such as vacuum deposition, spin coating, casting, Langmuir-Blodgett (LB), inkjet printing, laser printing, and/or laser induced thermal imaging (LITI).

When the hole transport region HTR includes a hole injection layer HIL and a hole transport layer HTL, the hole injection layer HIL may include any suitable hole injection material.

Examples of the hole injection material may include triphenylamine-containing polyether ketone (TPAPEK), 4-isopropyl-4'-methyldiphenyliodonium tetrakis (pentafluorophenyl) borate (PPBI), N, N'-diphenyl-N, N'-bis-[4-(phenyl-m-tolyl-amino)-phenyl]-phenyl-4,4'-diamine (DNTPD), phthalocyanine compounds (such as copper phthalocyanine), 4,4',4"-tris (3-methylphenylphenylamino) triphenylamine (m-MTDATA), N, N'-di (1-naphthyl)-N, N'-diphenylbenzidine (NPB), 4,4',4"-tris {N, N diphenylamino} triphenylamine (TDATA), 4,4',4"-tris (N, N-2-naphthylphenylamino) triphenylamine (2-TNATA), polyaniline/dodecyl benzene sulfonic acid (PANI/DBSA), poly (3,4-ethylenedioxythiophene)/poly (4-styrenesulfonate) (PEDOT/PSS), polyaniline/camphorsulfonic acid (PANI/CSA), polyaniline/poly (4-styrenesulfonate) (PANI/PSS), and the like. However, the embodiments of the present disclosure are not limited thereto.

When the hole transport region HTR includes a hole injection layer HIL and a hole transport layer HTL, the hole transport layer HTL may include any suitable hole transport material.

Examples of the hole transport material may include 1,1-bis [(di-4-thylamino) phenyl] cyclohexane (TAPC), N-phenyl carbazole, carbazole derivatives (such as polyvinyl carbazole), N, N'-bis (3-methylphenyl)-N, N'-diphenyl-[1,1-biphenyl]-4,4'-diamine (TPD), 4,4',4"-tris (N-carbazolyl) triphenylamine (TCTA), N, N'-di (1-naphthyl)-N, N'-diphenylbenzidine (NPB), and the like. However, the embodiments of the present disclosure are not limited thereto.

The thickness of the hole transport region HTR may be about 100 Å to about 10,000 Å, for example, about 100 Å to about 1,000 Å. When the hole transport region HTR includes both the hole injection layer HIL and the hole transport layer HTL, the thickness of the hole injection layer HIL may be about 100 Å to about 10,000 Å, for example, about 100 Å to about 1,000 Å, and the thickness of the hole transport layer HTL may be about 30 Å to about 1,000 Å.

When the thicknesses of the hole transport region HTR, the hole injection layer HIL and the hole transport layer HTL are within any of the above-described ranges, satisfactory (or suitable) hole transport characteristics may be obtained without substantial increase in driving voltage.

In addition to the above-mentioned materials, the hole transport region HTR may further include a charge-generating material for improving conductivity. The charge-generating material may be dispersed uniformly or non-uniformly in the hole transport region. The charge-generating material may be, for example, a p-dopant. The p-dopant may be, but is not limited to, one selected from a quinone derivative, a metal oxide, and a cyano group-containing compound. Non-limiting examples of the p-dopant may include quinone derivatives (such as tetracyanoquinodimethane (TCNQ) and/or 2,3,5,6-tetrafluoro-tetracyanoquinodimethane (F4-TCNQ)), metal oxides (such as tungsten oxide and/or molybdenum oxide), and the like.

As mentioned above, the hole transport region HTR may further include, in addition to the hole injection layer HIL and the hole transport layer HTL, at least one of a hole buffer layer or an electron blocking layer. The hole buffer layer may compensate a resonance distance depending on the wavelength of light emitted from the light emitting layer, so as to increase light emitting efficiency. The material included in the hole buffer layer may be any suitable material capable of being included in the hole transport region HTR. The electron blocking layer is a layer serving to prevent or reduce the electron injection from the electron transport region ETR to the hole transport region HTR.

The light emitting layer EML is provided on the hole transport region HTR. The thickness of the light emitting layer EML may be, for example, about 100 Å to about 600 Å. The light emitting layer EML may have a structure having a single layer composed of a single material, a single layer composed of a plurality of different material, or multiple layers composed of a plurality of different materials.

The light emitting layer EML may include the polycyclic compound according to an embodiment of the present disclosure described above. For example, the light emitting layer EML may include the polycyclic compound represented by Formula 1 below:

Formula 1

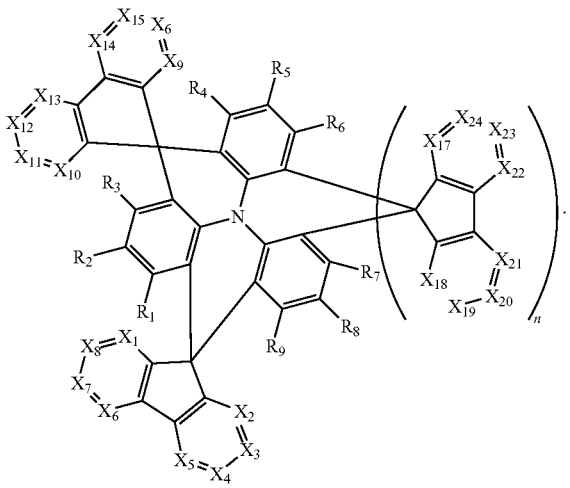

In Formula 1, $X_1$ to $X_{24}$ may be each independently $CR_{10}$ or N, and at least one of $X_1$ to $X_8$ and at least one of $X_9$ to $X_{16}$ may be N.

In Formula 1, $R_1$ to $R_9$ may be each independently hydrogen, deuterium, a halogen atom, a cyano group, a substituted or unsubstituted silyl group, a substituted or unsubstituted alkyl group having 1 or more and 12 or less carbon atoms, a substituted or unsubstituted aryl group having 6 or more and 30 or less ring carbon atoms; or a substituted or unsubstituted heteroaryl group having 2 or more and 30 or less ring carbon atoms.

$R_{10}$ may be hydrogen, deuterium, a halogen atom, a cyano group, a substituted or unsubstituted silyl group, a substituted or unsubstituted sulfonyl group, a substituted or unsubstituted alkyl group having 1 or more and 12 or less carbon atoms, a substituted or unsubstituted aryl group having 6 or more and 30 or less ring carbon atoms, or a substituted or unsubstituted heteroaryl group having 2 or more and 30 or less ring carbon atoms.

In Formula 1, n may be 0 or 1.

More detailed descriptions of $X_1$ to $X_{24}$, $R_1$ to $R_{10}$ and n in Formula 1 may be the same as provided above in connection with the polycyclic compound of an embodiment.

The light emitting layer EML may include at least one, for example, at least two polycyclic compounds represented by Formula 1.

The light emitting layer EML may include a compound represented by Formulae 1-1 or 1-2 below.

Formula 1-1

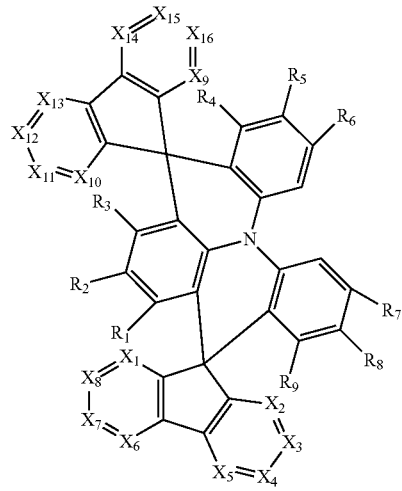

Formula 1-2

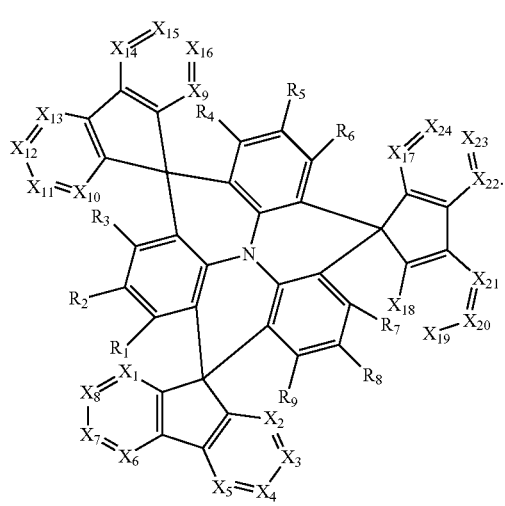

In Formula 1-1 and Formula 1-2, at least two of $X_1$ to $X_8$ and at least two of $X_9$ to $X_{16}$ may be N, for example, at least two of $X_1$, $X_2$, $X_9$ or $X_{10}$ may be N. $R_1$ to $R_9$ may be each independently hydrogen, and $R_{10}$ may be an unsubstituted methyl group or a methyl group substituted with a cyano group or a fluorine atom.

In Formula 1-2, at least one of $X_{17}$ to $X_{24}$ may be N, for example, at least one of $X_{17}$ or $X_{18}$ may be N.

In Formulae 1-1 and 1-2, definitions of $X_1$ to $X_{24}$, $R_1$ to $R_{10}$ and n may be the same contents as those provided in Formula 1 described above.

The light emitting layer EML may include at least one of the compounds represented by Compound Group 1 below:

Compound Group 1

1

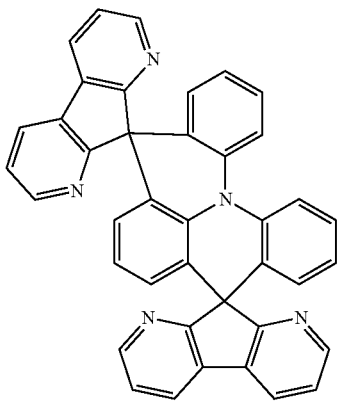

2

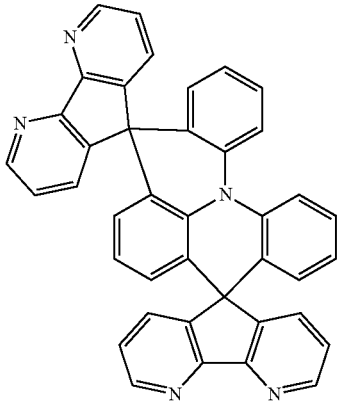

3

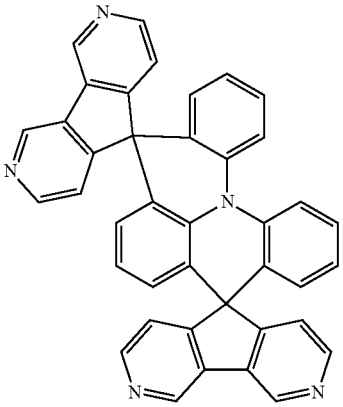

4
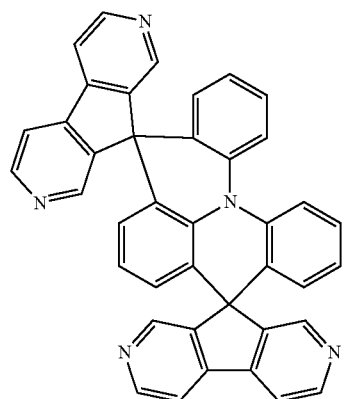
5
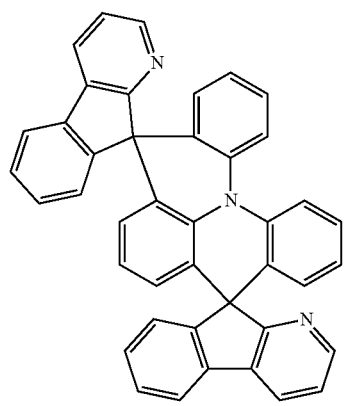
6
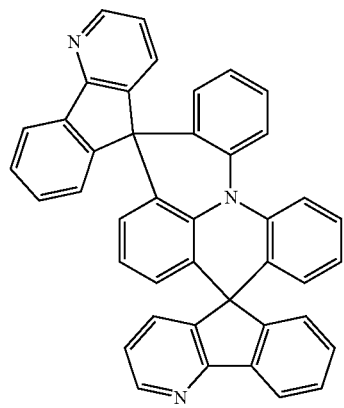
7
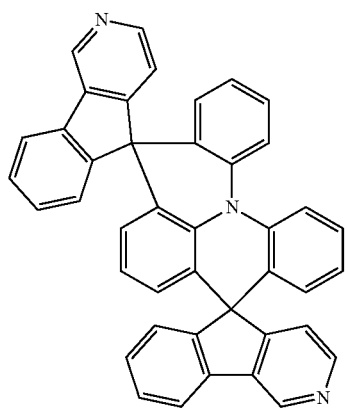
8
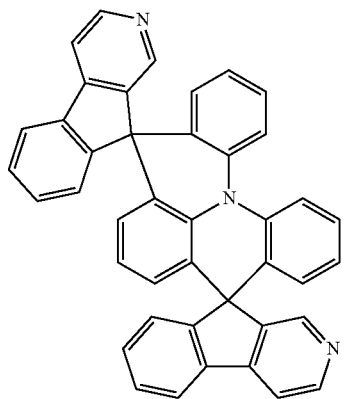
9
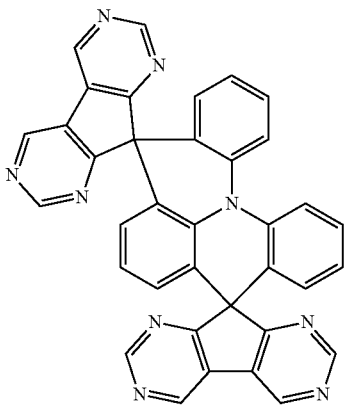
10
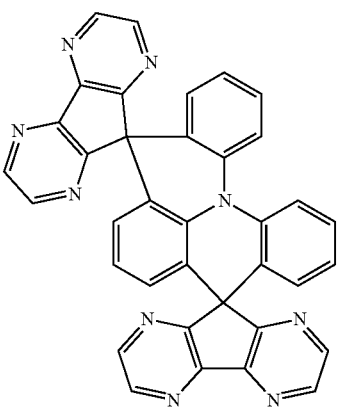
11
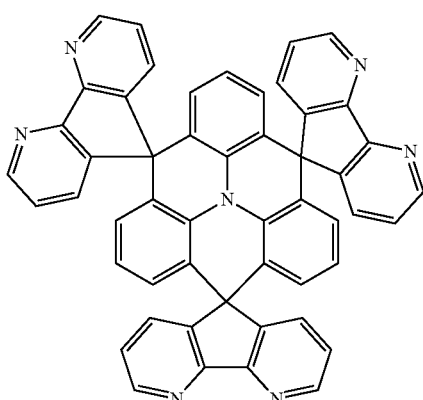

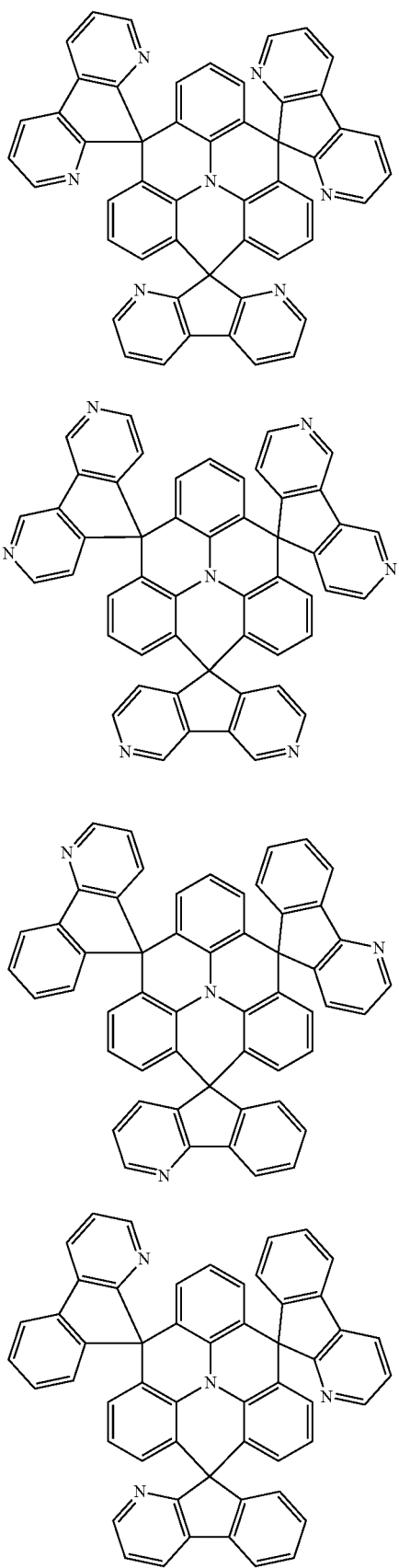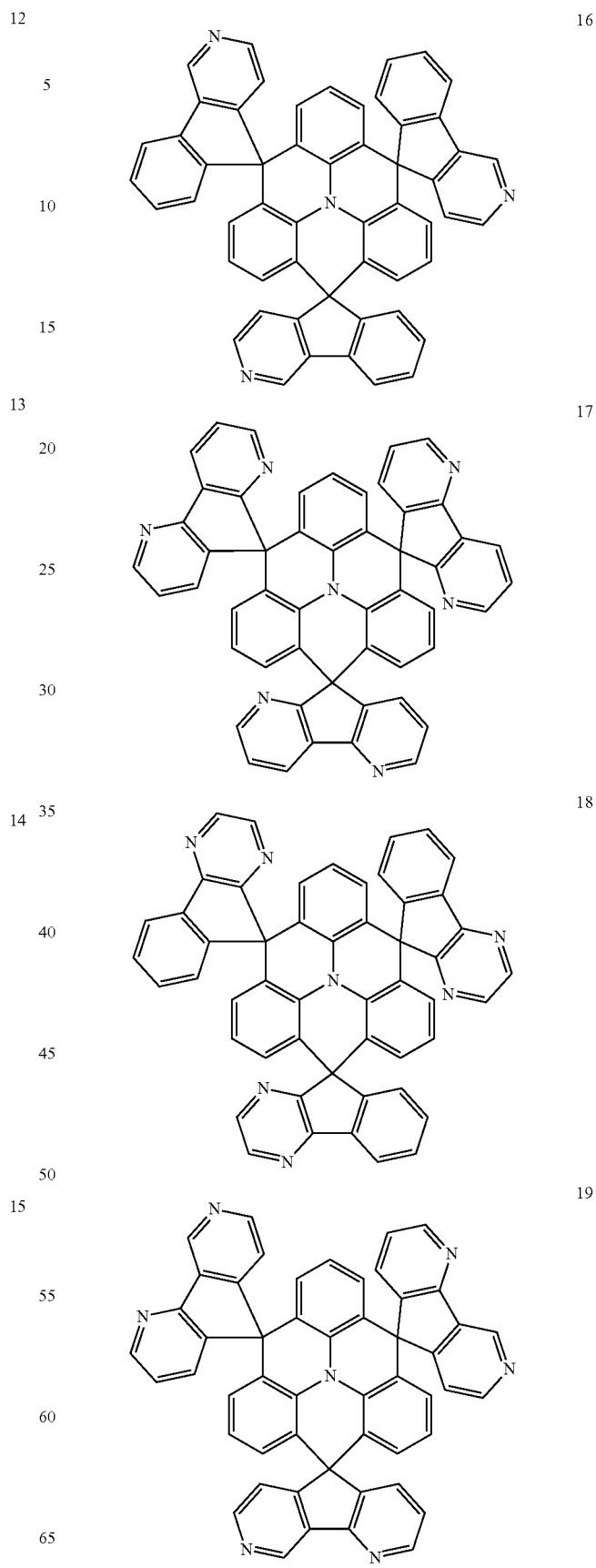

-continued

20
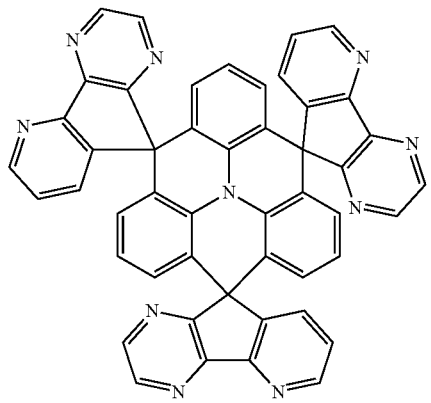

21
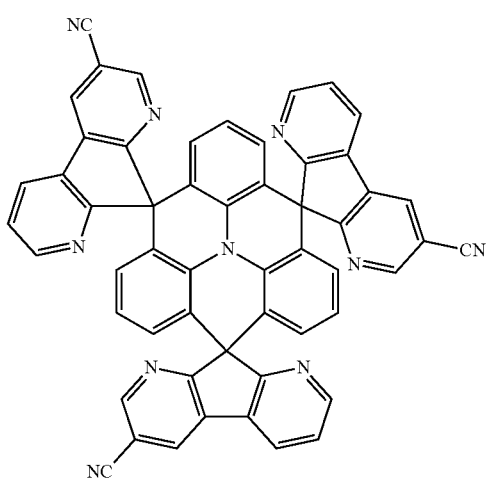

22
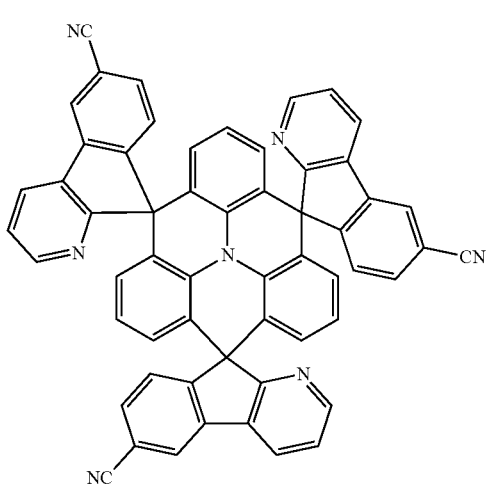

-continued

23
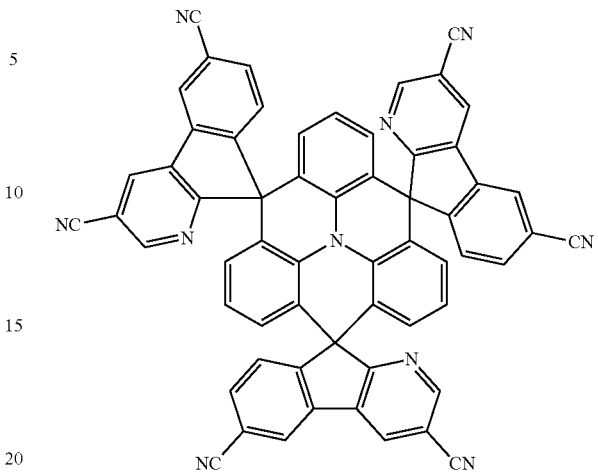

24
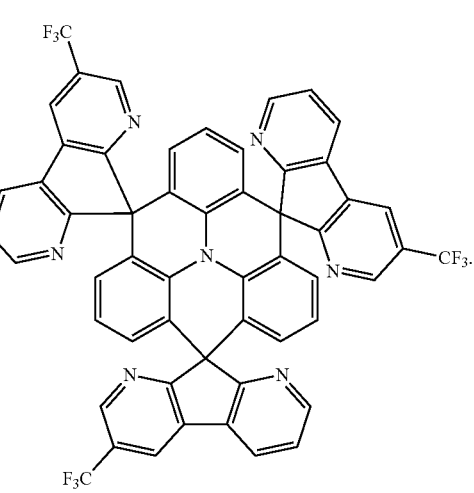

The light emitting layer EML may further include, in addition to the aromatic compound of the present embodiments, a suitable material. For example, the light emitting layer EML may further include a fluorescent material including any one selected from spiro-DPVBi, spiro-6P (2,2',7,7'-tetrakis (biphenyl-4-yl)-9,9'-spirobifluorene(spiro-sexiphenyl)), distyryl-benzene (DSB), distyryl-arylene (DSA), polyfluorene (PFO) based polymers, and poly (p-phenylene vinylene) (PPV) based polymers. However, the embodiments of the present disclosure are not limited thereby.

The polycyclic compound according to an embodiment of the present disclosure may be included in the light emitting layer EML to emit delayed fluorescence. For example, the polycyclic compound of an embodiment may be a delayed fluorescent material. The polycyclic compound of an embodiment represented by Formula 1 may be a thermally activated delayed fluorescence (TADF) dopant.

The organic electroluminescence device of an embodiment may include the polycyclic compound of an embodiment in the light emitting layer to improve light emitting efficiency. The organic electroluminescence device of an embodiment including the polycyclic compound of an embodiment may emit deep blue light. In addition, the polycyclic compound of an embodiment may be adjusted such that an energy gap between a singlet energy level and a triplet energy level is as small as 0.2 eV or less, and thus the organic electroluminescence device of an embodiment may allow thermally activated delayed fluorescence to efficiently emit.

The polycyclic compound of an embodiment may be a thermally activated delayed fluorescence material, which emits blue light. Accordingly, the light emitting layer EML of the organic electroluminescence device 10 of an embodiment, which includes the polycyclic compound of an embodiment, may emit blue light. The light emitting layer EML of the organic electroluminescence device 10 of an embodiment may emit deep blue light. The light emitting layer EML of the organic electroluminescence device 10 of an embodiment, which includes the polycyclic compound of an embodiment, may emit blue light having a wavelength range of about 440 nm to about 480 nm, about 440 nm to about 475 nm, about 440 nm to about 470 nm, or about 440 nm to about 450 nm.

The polycyclic compound according to an embodiment of the present disclosure may be included as a dopant material in the light emitting layer EML.

The light emitting layer EML may further include a host. The host is not particularly limited as long as it is a commonly used suitable material. Non-limiting examples of the host material include $Alq_3$(tris(8-hydroxyquinolino)aluminum), CBP(4,4'-bis(N-carbazolyl)-1,1'-biphenyl), PVK (poly(n-vinylcabazole), ADN(9,10-di(naphthalene-2-yl)anthracene), TCTA(4,4',4"-Tris(carbazol-9-yl)-triphenylamine), TPBi(1,3,5-tris(N-phenylbenzimidazole-2-yl)benzene), TBADN(3-tert-butyl-9,10-di(naphth-2-yl)anthracene), DSA(distyrylarylene), CDBP(4,4'-bis(9-carbazolyl)-2,2''-dimethyl-biphenyl), MADN(2-Methyl-9,10-bis(naphthalen-2-yl)anthracene), DPEPO (bis[2-(diphenylphosphino)phenyl] ether oxide), CP1 (hexaphenyl cyclotriphosphazene), UGH2 (1,4-Bis(triphenylsilyl)benzene), $DPSiO_3$ (Hexaphenylcyclotrisiloxane), $DPSiO_4$ (octaphenylcyclotetra siloxane), PPF (2,8-Bis(diphenylphosphoryl)dibenzofuran), mCP(1,3-Bis(N-carbazolyl)benzene), mCBP(3,3-Di(9H-carbazol-9-yl)biphenyl), and the like.

The polycyclic compound of an embodiment may have an absolute value of a difference between the singlet energy level and the triplet energy level of 0.2 eV or less. The polycyclic compound having a small gap between the singlet energy level and the triplet energy level may be included in the light emitting layer EML to allow thermally activated delayed fluorescence to effectively emit, so that the light emitting efficiency of the organic electroluminescence device of an embodiment may be improved.

The electron transport region ETR is provided on the light emitting layer EML. The electron transport region ETR may include, but is not limited to, at least one of a hole blocking layer, an electron transport layer ETL, or an electron injection layer EIL.

The electron transport region ETR may have a structure having a single layer composed of a single material, a single layer composed of a plurality of different materials, or multiple layers composed of a plurality of different materials.

For example, the electron transport region ETR may have a single layer structure of the electron injection layer EIL or the electron transport layer ETL, or may have a single structure composed of an electron injection material and an electron transport material. In some embodiments, the electron transport region ETR may have, but is not limited to, a single layer structure composed of a plurality of different materials, or a structure of the electron transport layer ETL/the electron injection layer EIL, the hole blocking layer/the electron transport layer ETL/the electron injection layer EIL, which are sequentially stacked form the first electrode EL1. The thickness of the electron transport region ETR may be, for example, about 1000 Å to about 1500 Å.

The electron transport region ETR may be formed by using one or more suitable methods such as vacuum deposition, spin coating, casting, Langmuir-Blodgett (LB), inkjet printing, laser printing, laser induced thermal imaging (LITI), and/or the like.

When the electron transport region ETR includes an electron transport layer ETL, the electron transport region ETR may include a suitable electron transport material. Examples of the material included in the electron transport region ETR may include, but are not limited to, $Alq_3$(Tris (8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, TPBi(1,3,5-tri(1-phenyl-1H-benzo[d]imidazol-2-yl)benzene), BCP(2,9-Dimethyl-4,7-diphenyl-1,10-phenanthroline), Bphen(4,7-Diphenyl-1,10-phenanthroline), TAZ(3-(4-Biphenylyl)-4-phenyl-5-tert-butylphenyl-1,2,4-triazole), NTAZ(4-(Naphthalen-1-yl)-3,5-diphenyl-4H-1,2,4-triazole), tBu-PBD(2-(4-Biphenylyl)-5-(4-tert-butylphenyl)-1,3,4-oxadiazole), BAlq(Bis(2-methyl-8-quinolinolato-N1,O8))-(1,1'-Biphenyl-4-olato)aluminum), Bebq2(berylliumbis (benzoquinolin-10-olate), ADN(9,10-di(naphthalene-2-yl) anthracene), and mixtures thereof.

When the electron transport region ETR includes an electron transport layer ETL, the thickness of the electron transport layer ETL may be about 100 Å to about 1000 Å, for example, about 150 Å to about 500 Å. When the thickness of electron transport layers ETL is within the above-mentioned range, satisfactory (or suitable) electron transport characteristics may be obtained without a substantial increase in driving voltage.

When the electron transport region ETR includes an electron injection layer EIL, the electron transport region ETR may include a suitable electron injection material. Examples of the material included in the electron transport region ETR may include, but are not limited to, a lanthanum group metal (such as LiF, lithium quinolate (LiQ), $Li_2O$, BaO, NaCl, CsF and/or Yb), a metal halide (such as RbCl and/or RbI), and the like. The electron injection layer EIL may be also made of a mixture of the electron injection material and an insulating organo metal salt. The organo metal salt may be a material having an energy band of about 4 eV or more. For example, the organo metal salt may include metal acetate, metal benzoate, metal acetoacetate, metal acetylacetonate, and/or metal stearate.

When the electron transport region ETR includes the electron injection layer EIL, the thickness of the electron injection layer EIL may be about 1 Å to about 100 Å, about 3 Å to about 90 Å. When the thickness of electron injection layers EIL is within the above-mentioned range, satisfactory (or suitable) electron injection characteristics may be obtained without a substantial increase in driving voltage.

The electron transport region ETR may include a hole blocking layer as described above. Examples of the hole blocking layer may include, but are not limited to, at least one of BCP (2,9-dimethyl-4,7-diphenyl-1,10-phenanthroline) or Bphen (4,7-diphenyl-1,10-phenanthroline).

The second electrode EL2 is provided on the electron transport region ETR. The second electrode EL2 has conductivity. The second electrode EL2 may be formed of a metal alloy or any suitable conductive compound. The second electrode EL2 may be a cathode. The second electrode EL2 may be a transmissive electrode, a semi-transmissive electrode, or a reflective electrode. When the second electrode EL2 is a transmissive electrode, the second electrode EL2 may be made of a transparent metal oxide such as an indium tin oxide (ITO), an indium zinc oxide (IZO), a zinc oxide (ZnO), an indium tin zinc oxide (ITZO), and/or the like.

When the second electrode EL2 is a semi-transmissive electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound or mixture thereof (e.g., a mixture of Ag and Mg). In some embodiments, the second electrode EL2 may have a multilayered structure including a reflective film or a semi-transmissive film formed of any of the above-exemplified materials, and a transparent conductive film formed of indium tin oxide (ITO), indium zinc oxide (IZO), zinc oxide (ZnO), indium tin zinc oxide (ITZO), and/or the like.

The second electrode EL2 may be connected (e.g., coupled) to an auxiliary electrode. When the second electrode EL2 is connected to the auxiliary electrode, the resistance of the second electrode EL2 may be reduced.

In the organic electroluminescence device 10, as a voltage is applied to the first electrode EL1 and the second electrode EL2, holes injected from the first electrode EL1 move to the light emitting layer EML via the hole transport region HTR, and electrons injected from the second electrode EL2 move to the light emitting layer EML via the electron transport region ETR. The holes and electrons are then recombined in the light emitting layer EML to generate excitons, and the exciton emit light when falling from the excited state to the ground state.

When the organic electroluminescence device 10 is a front light-emitting device, the first electrode EL1 may be a reflective electrode, and the second electrode EL2 may be a transmissive electrode or a semi-transmissive electrode. When the organic electroluminescence device 10 is a rear light-emitting device, the first electrode EL1 may be a transmissive electrode or a semi-transmissive electrode, and the second electrode EL2 may be a reflective electrode.

The organic electroluminescence device of an embodiment may include the polycyclic compound of an embodiment described above to improve luminescence. For example, the organic electroluminescence device of an embodiment may include the above-described polycyclic compound in the light emitting layer, to allow the polycyclic compound to emit light in the thermally activated delayed fluorescence process, so that high efficiency may be obtained. In some embodiments, the organic electroluminescence device according to an embodiment of the present disclosure may include the polycyclic compound of an embodiment in the light emitting layer, so that a highly efficient blue luminescence device may be secured through the thermally activated delayed fluorescence process.

Hereinafter, referring to Examples and Comparative Examples, the polycyclic compound according to an embodiment of the present disclosure and the organic electroluminescence device of an embodiment will be described in more detail. However, the following examples are only for the purpose of helping to understand the present invention, and the scope of the present invention is not limited thereto.

Examples

1. Synthesis of Polycyclic Compounds.

A method for synthesizing the polycyclic compounds according to embodiments of the present disclosure will be described with reference to the synthesis methods of Compound 1, Compound 2, Compound 11 and Compound 12 from Compound Group 1. However, the synthesis methods for polycyclic compounds described below are provided solely for purposes of illustration, and the synthesis method of polycyclic compounds according to an embodiment of the present disclosure is not limited to the following examples.

Synthesis of Compound 1

2,2'-dibromotriphenylamine (1.0 g) and tetrahydrofuran (THF) (20 ml) were added to a reaction vessel which had been substituted with argon, the mixture was cooled to −20° C., and i-PrMgCl.LiCl and 3.8 mL of a THF solution (1.3 M) were added dropwise thereto. The resulting mixture was continuously stirred for 30 minutes after the dropwise addition, 1,8-diazafluoren-9-one (0.95 g), and a THF solution (20 mL) were added dropwise thereto, and then stirring was performed for 24 hours. Thereafter, water was added after air cooling to separate an organic layer, and a solvent was removed. The obtained crude product was purified by silica gel column chromatography (using a solvent of ethyl acetate) and then recrystallized with a toluene/hexane mixture solvent to obtain 1.5 g of solid Compound A.

Thereafter, Compound A was dissolved in 30 mL of dichloromethane, 1 mL of Eaton reagent was added, and the mixture was stirred for 24 hours at room temperature. After air cooling, water and sodium bicarbonate were added to separate the organic layer, and the solvent was removed. The obtained crude product was purified by silica gel column chromatography (using a solvent of ethyl acetate) and then recrystallized with the toluene/hexane mixture solvent to obtain 0.91 g (yield 60%) of target Compound 1 as a pale yellow solid. The molecular weight of Compound 1 measured by Fast Atom Bombardment-Mass Spectrometry (FAB-MS) measurement was 573.

Synthesis of Compound 2

2,2'-dibromotriphenylamine (1.0 g) and tetrahydrofuran (THF) (20 ml) were added to a reaction vessel which had been substituted with argon, the mixture was cooled to −20° C., and i-PrMgCl.LiCl and 3.8 mL of a THF solution (1.3 M) were added dropwise thereto. The resulting mixture was continuously stirred for 30 minutes after the dropwise addition, 4,5-diazafluoren-9-one (0.95 g) and a THF solution (20 mL) were then added dropwise thereto, and then stirring was performed for 24 hours. Thereafter, water was added after air cooling to separate an organic layer and to remove a solvent. The obtained crude product was purified by silica gel column chromatography (using a solvent of ethyl acetate) and then recrystallized with a toluene/hexane mixture solvent to obtain 1.5 g of solid Compound B.

Thereafter, Compound B was dissolved in 30 mL of dichloromethane, 1 mL of Eaton reagent was added, and the mixture was stirred for 24 hours at room temperature. After air cooling, water and sodium bicarbonate were added to separate the organic layer, and the solvent was removed. The obtained crude product was purified by silica gel column chromatography (using a solvent of ethyl acetate) and then recrystallized with the toluene/hexane mixture solvent to obtain 0.91 g (yield 65%) of target Compound 2 as a pale yellow solid. The molecular weight of Compound 2 measured by FAB-MS measurement was 573.

Synthesis of Compound 12

2,2',2''-tribromotriphenylamine (1.0 g) and tetrahydrofuran (THF) (20 ml) were added to a reaction vessel which had been substituted with argon, the mixture was cooled to −20° C., and i-PrMgCl.LiCl and 4.8 mL of a THF solution (1.3 M) were added dropwise thereto. The resulting mixture was continuously stirred for 30 minutes after the dropwise addition, 1,8-diazafluoren-9-one (1.19 g) and a THF solution (20 mL) were then added dropwise thereto, and then stirring was performed for 24 hours. Thereafter, water was added after air cooling to separate an organic layer and to remove a solvent. The obtained crude product was purified by silica gel column chromatography (using a solvent of ethyl acetate) and then recrystallized with a toluene/hexane mixture solvent to obtain 1.5 g of solid Compound C.

Thereafter, Compound C was dissolved in 30 mL of dichloromethane, 1 mL of Eaton reagent was added, and the mixture was stirred for 24 hours at room temperature. After air cooling, water and sodium bicarbonate were added to separate the organic layer, and the solvent was removed. The obtained crude product was purified by silica gel column chromatography (using a solvent of ethyl acetate) and then recrystallized with the toluene/hexane mixture solvent to obtain 0.42 g (yield 25%) of target Compound 12 as a pale yellow solid. The molecular weight of Compound 12 measured by FAB-MS measurement was 737.

Synthesis of Compound 11

2,2',2"-tribromotriphenylamine (1.0 g) and tetrahydrofuran (THF) (20 ml) were added to a reaction vessel which had been substituted with argon, the mixture was cooled to −20° C., and i-PrMgCl.LiCl and 4.8 mL of a THF solution (1.3 M) were added dropwise thereto. The resulting mixture was continuously stirred for 30 minutes after the dropwise addition, 4,5-diazafluoren-9-one (1.19 g) and a THF solution (20 mL) were added dropwise thereto, and then stirring was performed for 24 hours. Thereafter, water was added after air cooling to separate an organic layer and to remove a solvent. The obtained crude product was purified by silica gel column chromatography (using a solvent of ethyl acetate) and then recrystallized with a toluene/hexane mixture solvent to obtain 1.5 g of solid Compound D.

Thereafter, Compound D was dissolved in 30 mL of dichloromethane, 1 mL of Eaton reagent was added, and the mixture was stirred for 24 hours at room temperature. After air cooling, water and sodium bicarbonate were added to separate the organic layer, and the solvent was removed. The obtained crude product was purified by silica gel column chromatography (using a solvent of ethyl acetate) and then recrystallized with the toluene/hexane mixture solvent to obtain 0.42 g (yield 32%) of target Compound 11 as a pale yellow solid. The molecular weight of Compound 11 measured by FAB-MS measurement was 737.

2. Production and Evaluation of an Organic Electroluminescence Device Including the Polycyclic Compound.

Production of Organic Electroluminescence Device

The organic electroluminescence device of an embodiment including the polycyclic compound of an embodiment in the light emitting layer was produced by the following method. Compound 1 and Compound 12 described above were used as the light emitting layer material to produce the organic electroluminescence device of Example 1 and Example 2, respectively. In Comparative Examples 1 to 6, Comparative Example Compounds C1 to C6 illustrated below were used as light emitting layer materials to produce the respective organic electroluminescence device.

The compounds used for forming a light emitting layer in Examples 1 and 2, and Comparative Examples 1 to 6 are shown in Table 1.

TABLE 1

Compound 1

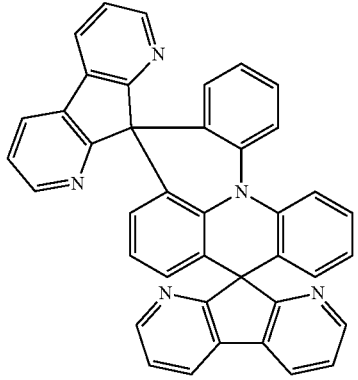 [SMILES: c1cnc2c(c1)-c1cccnc1C21c2ccccc2N2c3ccccc3C3(c4cccc1c42)c1ncccc1-c1cccnc13]

Compound 12

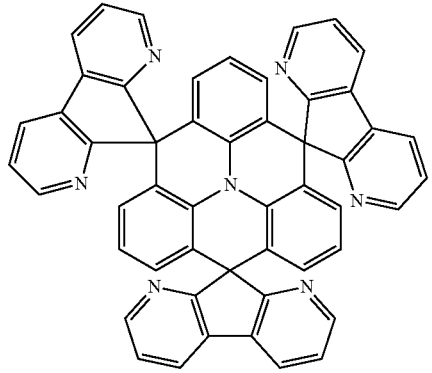 [SMILES: c1cnc2c(c1)-c1cccnc1C21c2cccc3c2N2c4c1cccc4C1(c4cccc(c42)C32c3ncccc3-c3cccnc32)c2ncccc2-c2cccnc21]

TABLE 1-continued
| | |
|---|---|
| Comparative Example Compound C1 | 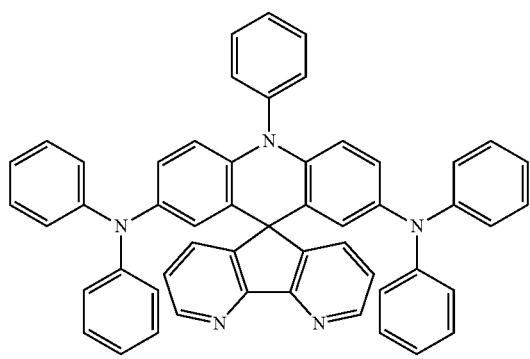 [SMILES: c1ccc(N(c2ccccc2)c2ccc3c(c2)C2(c4cc(N(c5ccccc5)c5ccccc5)ccc4N3c3ccccc3)c3cccnc3-c3ncccc32)cc1] |
| Comparative Example Compound C2 | 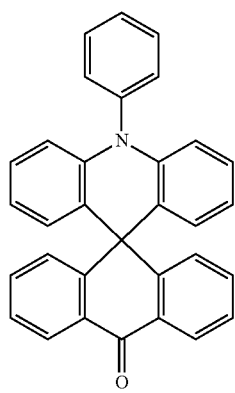 [SMILES: O=C1c2ccccc2C2(c3ccccc31)c1ccccc1N(c1ccccc1)c1ccccc12] |
| Comparative Example Compound C3 | 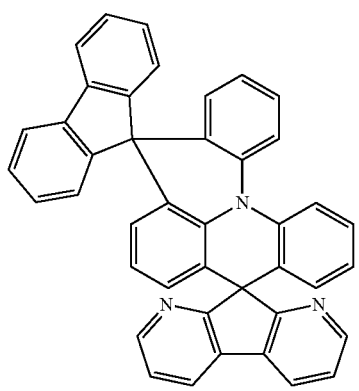 [SMILES: c1ccc2c(c1)-c1ccccc1C21c2ccccc2N2c3ccccc3C3(c4cccc1c42)c1ncccc1-c1cccnc13] |
| Comparative Example Compound C4 | 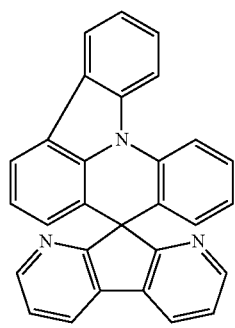 [SMILES: c1cnc2c(c1)-c1cccnc1C21c2ccccc2-n2c3ccccc3c3cccc1c32] |

TABLE 1-continued

Comparative Example Compound C5

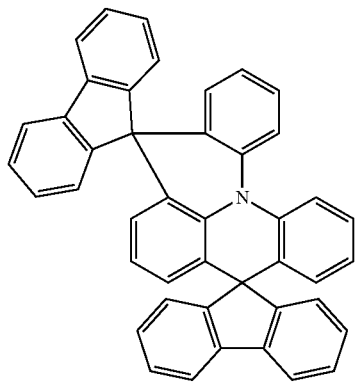 [SMILES: c1ccc2c(c1)-c1ccccc1C21c2ccccc2N2c3ccccc3C3(c4ccccc4-c4ccccc43)c3cccc1c32]

Comparative Example Compound C6

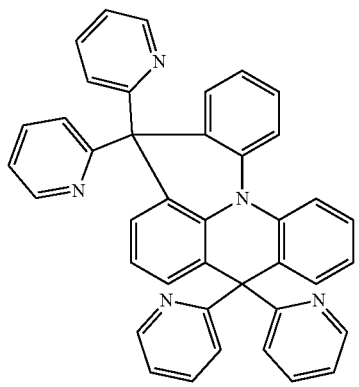 [SMILES: c1ccc(C2(c3ccccn3)c3ccccc3N3c4ccccc4C(c4ccccn4)(c4ccccn4)c4cccc2c43)nc1]

The organic electroluminescence devices of Examples and Comparative Examples were produced by the following method.

ITO having a thickness of 150 nm was patterned on a glass substrate, followed by washing with ultrapure water and performing UV ozone treatment for 10 minutes. Thereafter, the hole injection layer having a thickness of 10 nm was formed with HAT-CN, and the hole transport layer having a thickness of 80 nm was formed with NPD. Next, the electron blocking layer having a thickness of 5 nm was formed with mCP.

Next, in the light emitting layer, the polycyclic compound (Compound 1 or Compound 12) of an embodiment and DPEPO were co-deposited at a ratio of 20:80. The thickness of the light emitting layer was 20 nm. Thereafter, the hole blocking layer having a thickness of 20 nm was formed with DPEPO, the electron transport layer having a thickness of 30 nm was formed with TPBi, and the electron injection layer having a thickness of 0.5 nm was formed with LiF. Next, the second electrode having a thickness of 100 nm was formed with aluminum (Al).

In Examples, the hole injection layer, the hole transport layer, the electron blocking layer, the light emitting layer, the hole blocking layer, the electron transport layer, the electron injection layer, and the second electrode were formed by using a vacuum deposition apparatus.

In Comparative Examples 1 to 6, the organic electroluminescence device was produced in the same (or substantially the same) manner as in the production method of the organic electroluminescence devices of the Examples, except that Comparative Example Compounds C1 to C6 and DPEPO were used at a ratio of 20:80 in the light emitting layer, instead of Compounds 1 and 12.

Evaluation of Characteristics of Organic Electroluminescence

In order to evaluate the characteristics of the organic electroluminescence device according to Examples and Comparative Examples, the external quantum efficiency (EQE) and the half life at a maximum emission wavelength ($\lambda_{max}$) and at a current density of 10 mA/cm$^2$ were measured. The maximum emission wavelength of light emitting spectrum was measured by depositing a sample of a subject compound on a quartz glass plate at room temperature (about 300 K). The external quantum efficiency was measured by using Hamamatsu Photonics' external quantum efficiency measuring device C9920-12. The luminance half life was measured relative to the initial luminance of 100 cd/m$^2$, and the half life of Example 1 is represented as a relative ratio based on 1.0.

The evaluation results on the characteristics of the organic electroluminescence devices of Examples and Comparative Examples are shown in Table 2.

TABLE 2

| Classification | Dopant of light emitting layer | $\lambda_{max}$ (nm) | EQE (%) | Life LT$_{50}$ |
|---|---|---|---|---|
| Example 1 | Compound 1 | 462 | 17.2 | 1.0 |
| Example 2 | Compound 12 | 455 | 16.6 | 1.2 |
| Comparative Example 1 | Comparative Example Compound C1 | 510 | 9.6 | 0.20 |
| Comparative Example 2 | Comparative Example Compound C2 | 490 | 14.2 | 0.31 |

TABLE 2-continued

| Classification | Dopant of light emitting layer | $\lambda_{max}$ (nm) | EQE (%) | Life $LT_{50}$ |
|---|---|---|---|---|
| Comparative Example 3 | Comparative Example Compound C3 | 466 | 10.1 | 0.21 |
| Comparative Example 4 | Comparative Example Compound C4 | 470 | 8.2 | 0.87 |
| Comparative Example 5 | Comparative Example Compound C5 | 420 | 0.5 | 0.11 |
| Comparative Example 6 | Comparative Example Compound C6 | 445 | 4.7 | 0.39 |

In Examples 1 and 2, the organic electroluminescence devices included Compounds 1 and 12 as dopants of the light emitting layer, respectively. In Comparative Examples 1 to 6, the organic electroluminescence devices included Comparative Example Compounds C1 to C6 as dopants of the light emitting layer, respectively.

Referring to Table 2, it may be seen that the organic electroluminescence devices of Examples 1 and 2 have higher efficiency than the organic electroluminescence devices of Comparative Examples 1 to 6. Without being bound by any particular theory, it is believed that the organic electroluminescence devices of Examples 1 and 2 disperse the charge transfer in two or three azafluorene rings, as in the case of Compounds 1 and 12, for example, thereby having a longer life than the organic electroluminescence devices of Comparative Examples 1 to 6.

The organic electroluminescence device of an embodiment of the present disclosure may include the polycyclic compound of an embodiment described above in the light emitting layer, in order to obtain high light emitting efficiency. The polycyclic compound of an embodiment may be used as a thermally activated delayed fluorescence material, which emits blue light, to improve the blue light emitting efficiency of the organic electroluminescence device. Further, in the organic electroluminescence device of an embodiment, the polycyclic compound represented by Formula 1 may be substituted so as to obtain improved blue light emission, high external quantum efficiency, and long life.

The polycyclic compound of an embodiment may improve the light emitting efficiency of an organic electroluminescence device.

The organic electroluminescence device of an embodiment may include the polycyclic compound of an embodiment in the light emitting layer to obtain high efficiency.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

In addition, the terms "substantially," "about," and similar terms are used as terms of approximation and not as terms of degree, and are intended to account for the inherent deviations in measured or calculated values that would be recognized by those of ordinary skill in the art.

While the present invention has been particularly shown and described with reference to example embodiments thereof, it will be understood by those skilled in the art that various changes in form and details may be made therein without departing from the spirit and scope of the invention as defined in the following claims and equivalents thereof.

Therefore, the technical scope of the present invention should not be limited to the contents described in the detailed description of the specification, but should be defined by the claims and their equivalents.

What is claimed is:

1. A polycyclic compound represented by Formula 1 below:

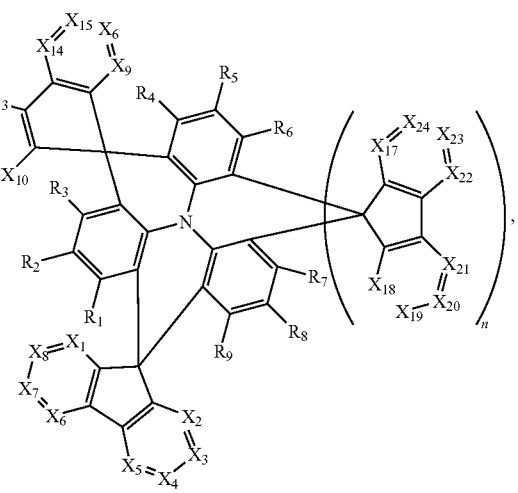

Formula 1 wherein in Formula 1, $X_1$ to $X_{24}$ are each independently $CR_{10}$ or N;

at least one of $X_1$ to $X_8$ and at least one of $X_9$ to $X_{16}$ is N;

$R_1$ to $R_9$ are each independently selected from hydrogen, deuterium, a halogen atom, a cyano group, a substituted or unsubstituted silyl group, a substituted or unsubstituted alkyl group having 1 to 12 carbon atoms, a substituted or unsubstituted aryl group having 6 to 30 ring carbon atoms, and a substituted or unsubstituted heteroaryl group having 2 to 30 ring carbon atoms;

$R_{10}$ is selected from hydrogen, deuterium, a halogen atom, a cyano group, a substituted or unsubstituted silyl group, a substituted or unsubstituted sulfonyl group, a substituted or unsubstituted alkyl group having 1 to 12 carbon atoms, a substituted or unsubstituted aryl group having 6 to 30 ring carbon atoms, and a substituted or unsubstituted heteroaryl group having 2 to 30 ring carbon atoms; and n is 0 or 1.

2. The polycyclic compound of claim 1, wherein the polycyclic compound of Formula 1 is represented by Formula 1-1 below or Formula 1-2 below:

Formula 1-1

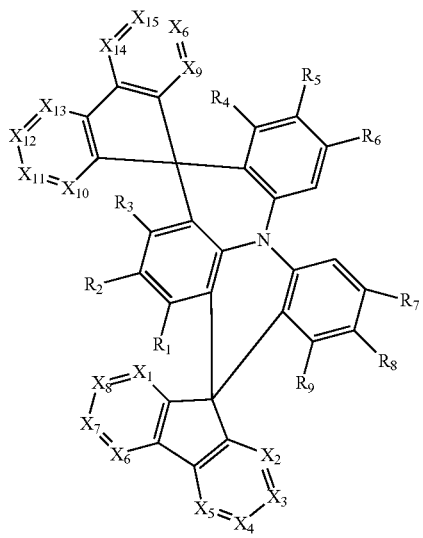

Formula 1-2

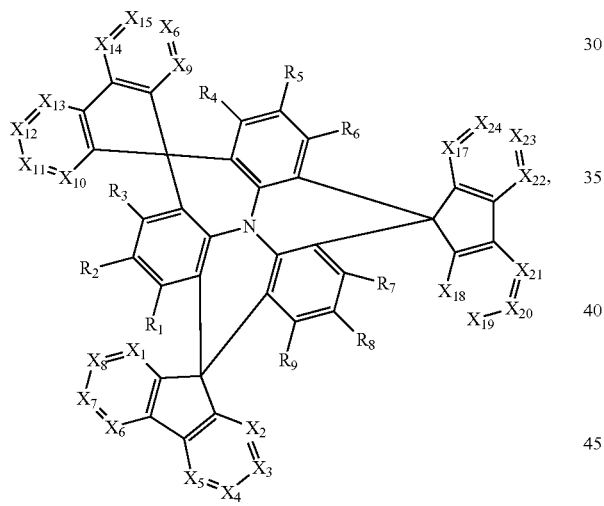

wherein in Formula 1-1 and Formula 1-2,
$X_1$ to $X_{24}$, and $R_1$ to $R_{10}$ are the same as defined in Formula 1.

3. The polycyclic compound of claim 1, wherein at least two of $X_1$ to $X_8$ and at least two of $X_9$ to $X_{16}$ are N.

4. The polycyclic compound of claim 1, wherein when n is 1, at least one of $X_{17}$ to $X_{24}$ is N.

5. The polycyclic compound of claim 1, wherein when n is 1, at least two of $X_{17}$ to $X_{24}$ are N.

6. The polycyclic compound of claim 1, wherein at least two of $X_1$, $X_2$, $X_9$ or $X_{10}$ are N.

7. The polycyclic compound of claim 1, wherein $X_1$, $X_2$, $X_9$ and $X_{10}$ are each N.

8. The polycyclic compound of claim 1, wherein when n is 1, at least one of $X_{17}$ or $X_{18}$ is N.

9. The polycyclic compound of claim 1, wherein $R_1$ to $R_9$ are each hydrogen.

10. The polycyclic compound of claim 1, wherein $R_{10}$ is an unsubstituted methyl group or a methyl group substituted with a cyano group or a fluorine atom.

11. The polycyclic compound of claim 1, wherein the polycyclic compound of Formula 1 is one selected from Compounds 1 to 24, collectively denoted as Compound Group 1:

Compound Group 1

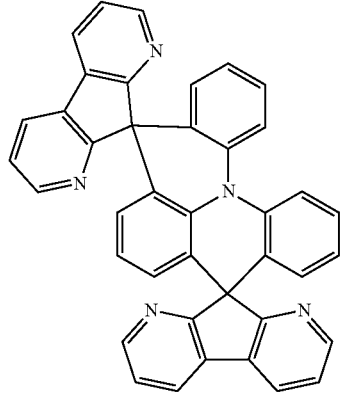

1

2

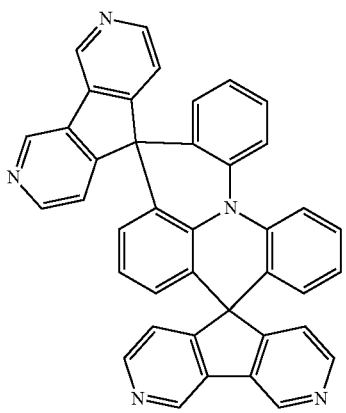

3

-continued
4
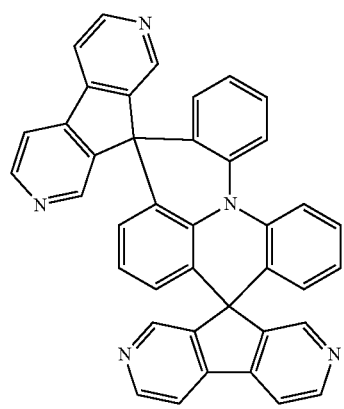
5
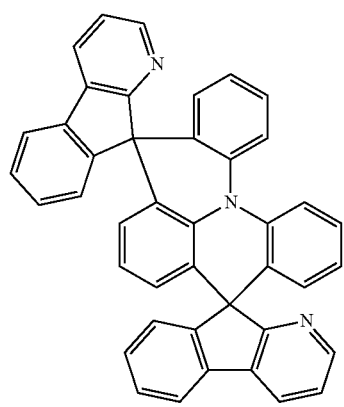
6
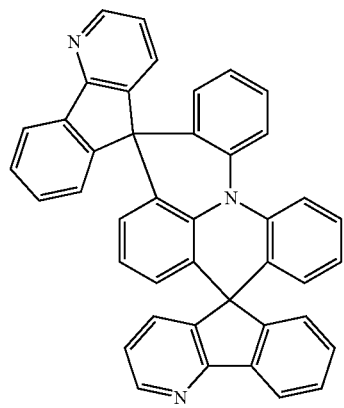
7
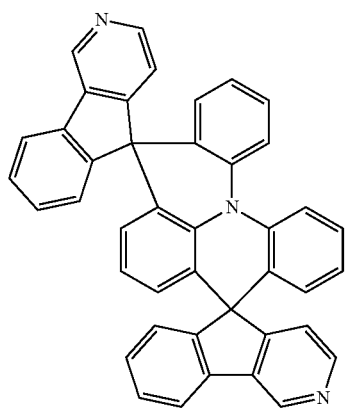
-continued
8
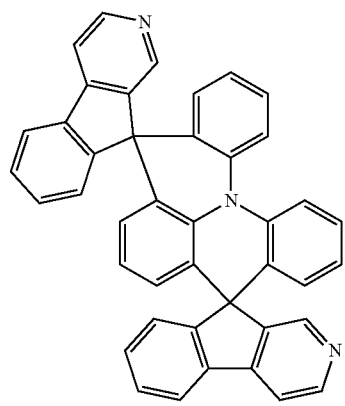
9
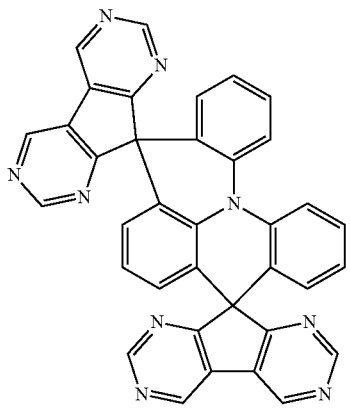
10
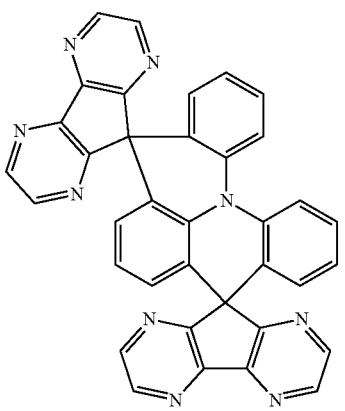
11
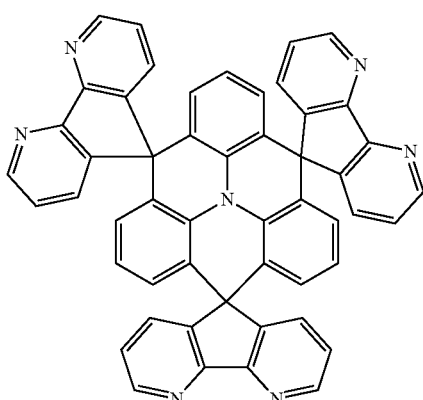

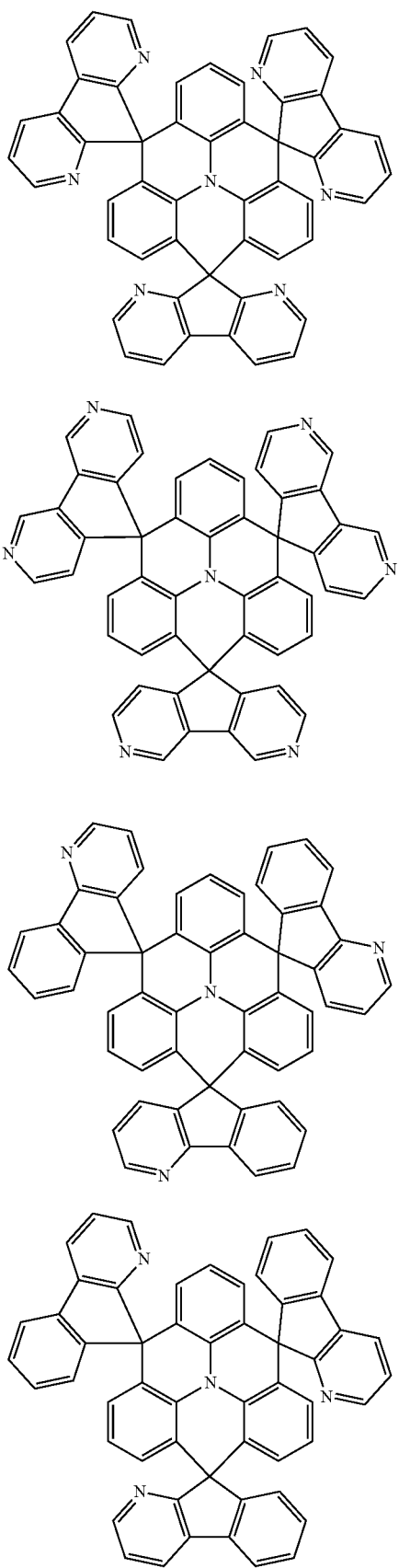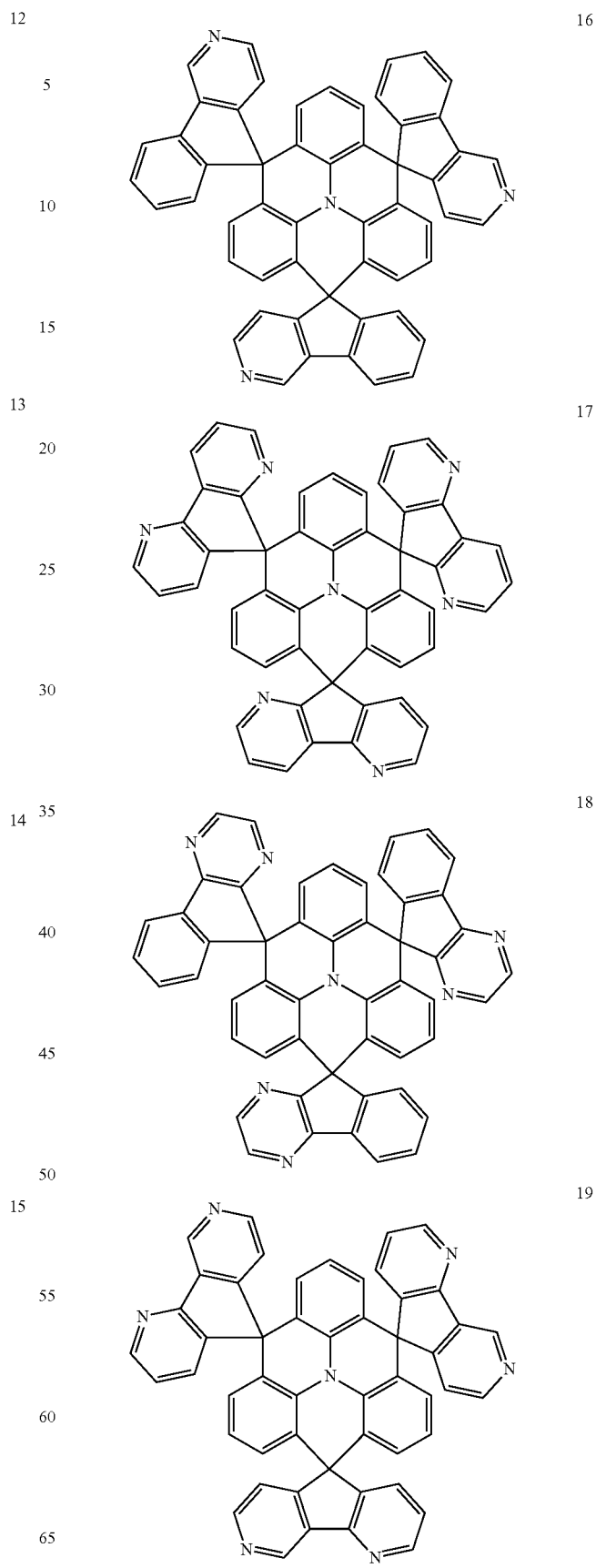

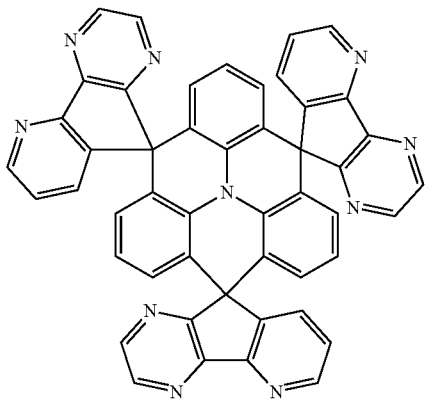
20

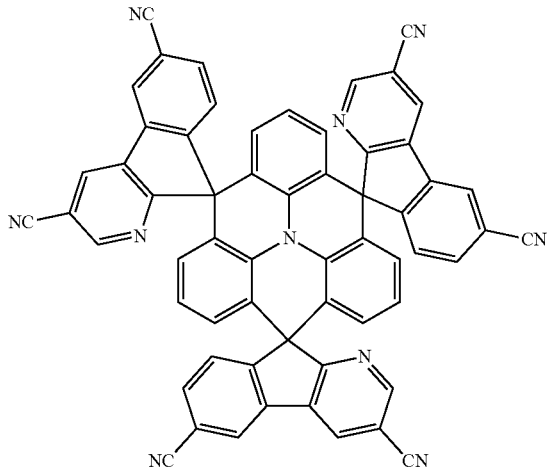
23

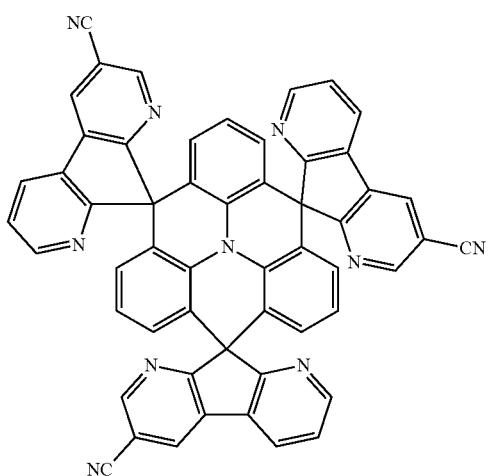
21

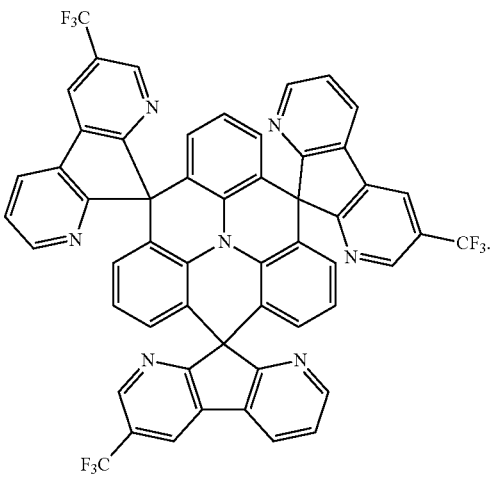
24

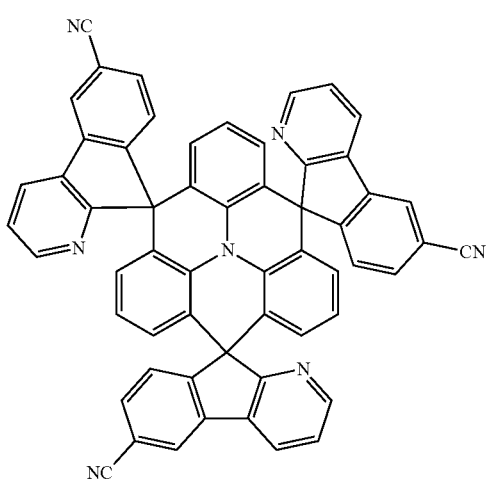
22

12. An organic electroluminescence device comprising:
a first electrode;
a hole transport region on the first electrode;
a light emitting layer on the hole transport region;
an electron transport region on the light emitting layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide of one or more thereof,
wherein the light emitting layer comprises a polycyclic compound represented by Formula 1:

Formula 1

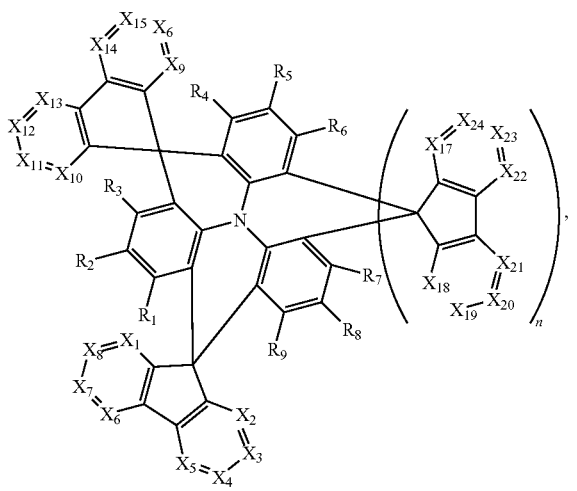

wherein in Formula 1,
X$_1$ to X$_{24}$ are each independently CR$_{10}$ or N;
at least one of X$_1$ to X$_8$ and at least one of X$_9$ to X$_{16}$ is N;
R$_1$ to R$_9$ are each independently selected from hydrogen, deuterium, a halogen atom, a cyano group, a substituted or unsubstituted silyl group, a substituted or unsubstituted alkyl group having 1 to 12 carbon atoms, a substituted or unsubstituted aryl group having 6 to 30 ring carbon atoms, and a substituted or unsubstituted heteroaryl group having 2 to 30 ring carbon atoms;
R$_{10}$ is selected from hydrogen, deuterium, a halogen atom, a cyano group, a substituted or unsubstituted silyl group, a substituted or unsubstituted sulfonyl group, a substituted or unsubstituted alkyl group having 1 to 12 carbon atoms, a substituted or unsubstituted aryl group having 6 to 30 ring carbon atoms, and a substituted or unsubstituted heteroaryl group having 2 to 30 ring carbon atoms; and
n is 0 or 1.

13. The organic electroluminescence device of claim 12, wherein the light emitting layer is for emitting blue light.

14. The organic electroluminescence device of claim 12, wherein the light emitting layer is a fluorescent light emitting layer comprising a host and a dopant, and the dopant comprises the polycyclic compound represented by Formula 1.

15. The organic electroluminescence device of claim 12, wherein the polycyclic compound represented by Formula 1 is a thermally activated delayed fluorescence compound.

16. The organic electroluminescence device of claim 12, wherein the polycyclic compound represented by Formula 1 is a thermally activated delayed fluorescence dopant.

17. The organic electroluminescence device of claim 12, wherein, in the polycyclic compound represented by Formula 1, an absolute value of a difference between a singlet energy level and a triplet energy level is 0.2 eV or less.

18. The organic electroluminescence device of claim 12, wherein at least two of X$_1$ to X$_8$ and at least two of X$_9$ to X$_{16}$ are N.

19. The organic electroluminescence device of claim 12, wherein when n is 1, at least one of X$_{17}$ to X$_{24}$ is N.

20. The organic electroluminescence device of claim 12, wherein at least two of X$_1$, X$_2$, X$_9$ or X$_{10}$ are N.

21. The organic electroluminescence device of claim 12, wherein the light emitting layer comprises at least one of Compounds 1 to 24, collectively denoted as Compound Group 1:

Compound Group 1

1

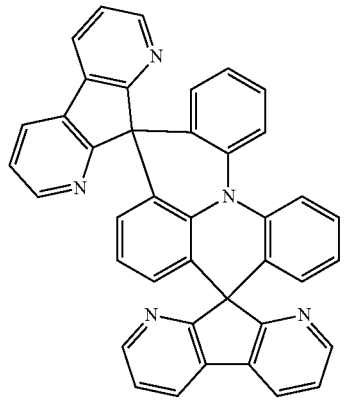

2

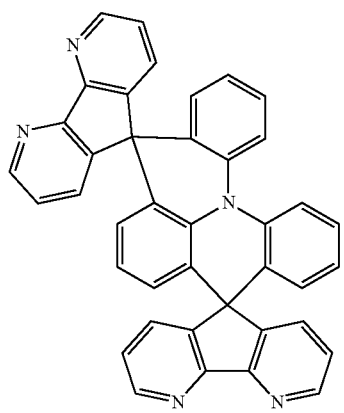

3

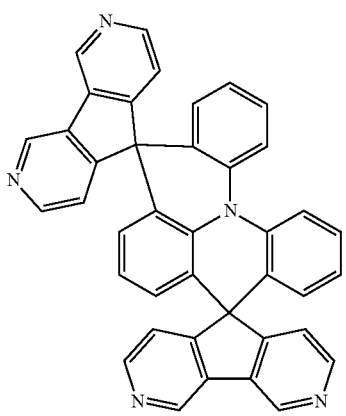

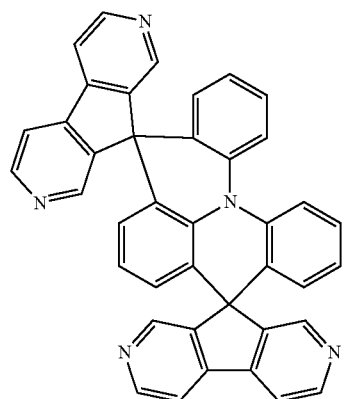
4
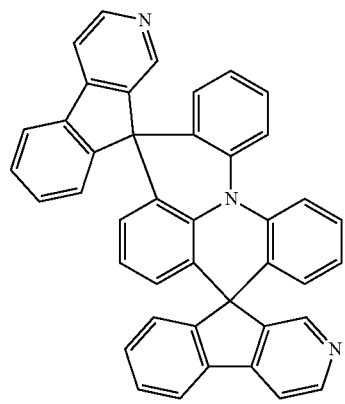
8
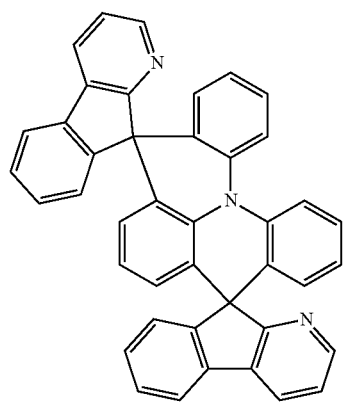
5
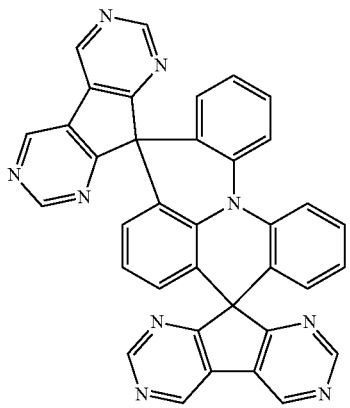
9
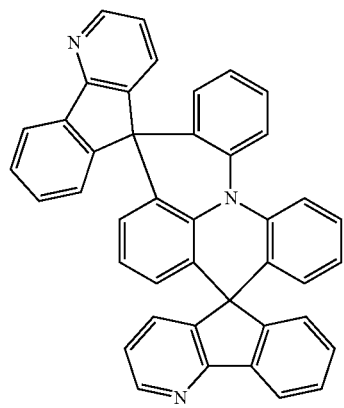
6
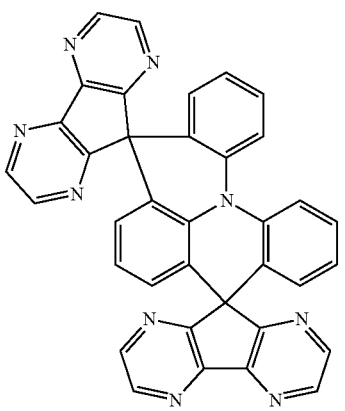
10
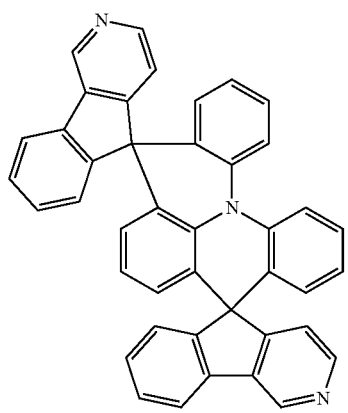
7
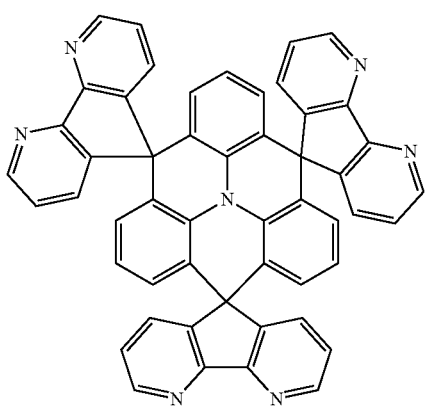
11

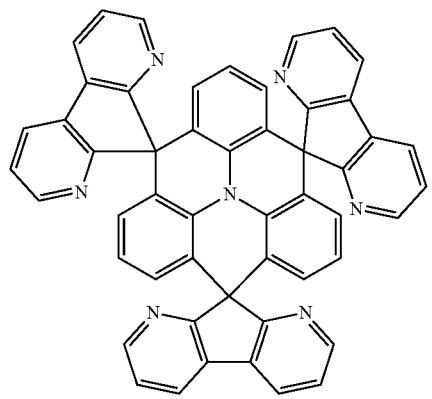
12
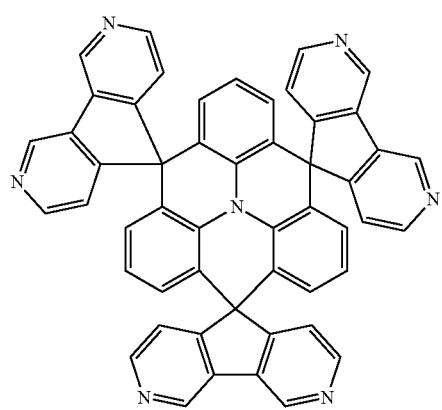
13
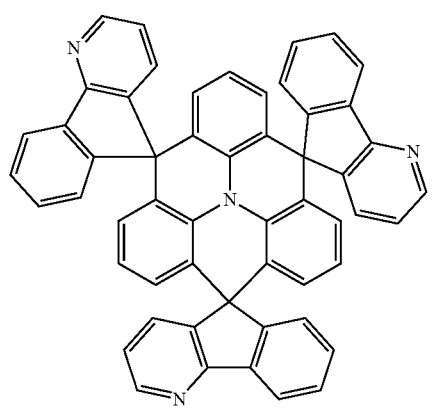
14
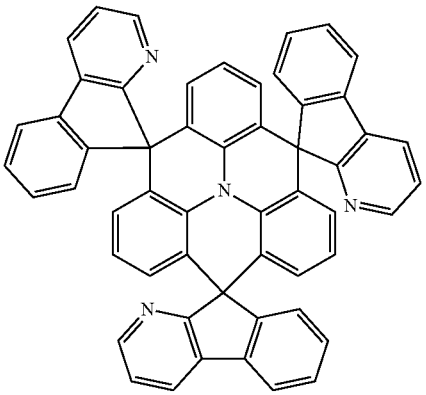
15
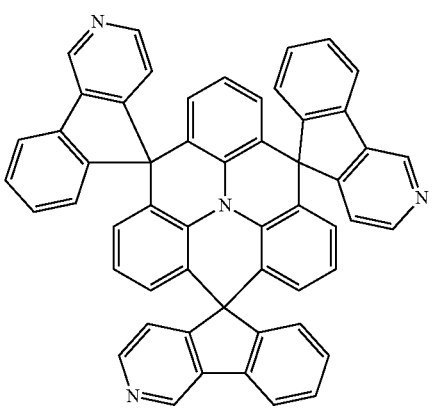
16
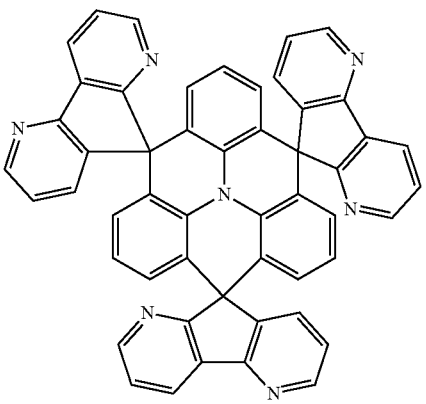
17
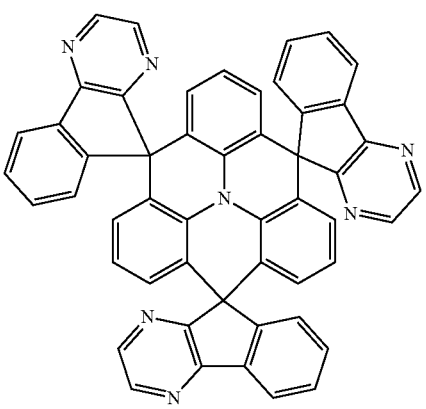
18

19
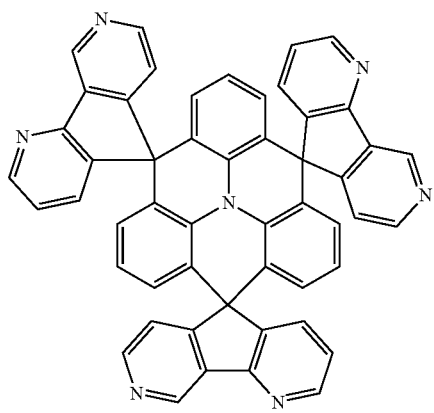
20
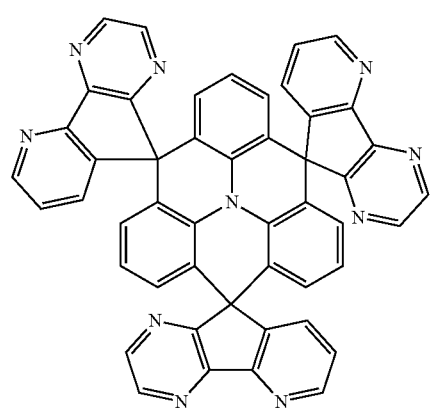
21
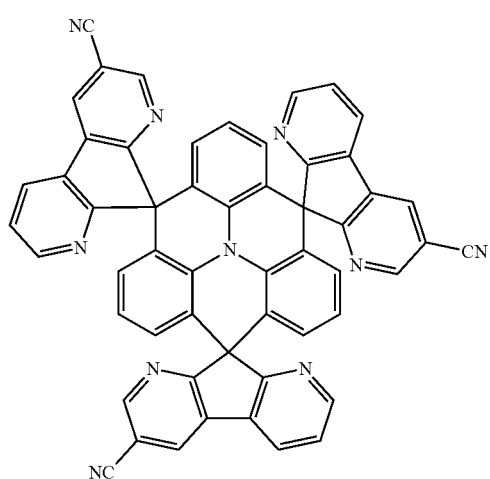
22
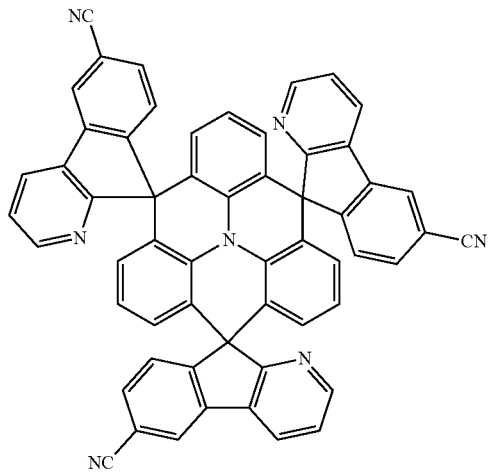
23
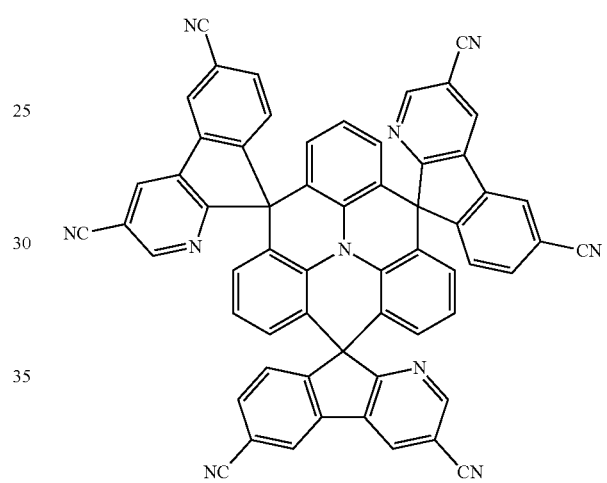
24
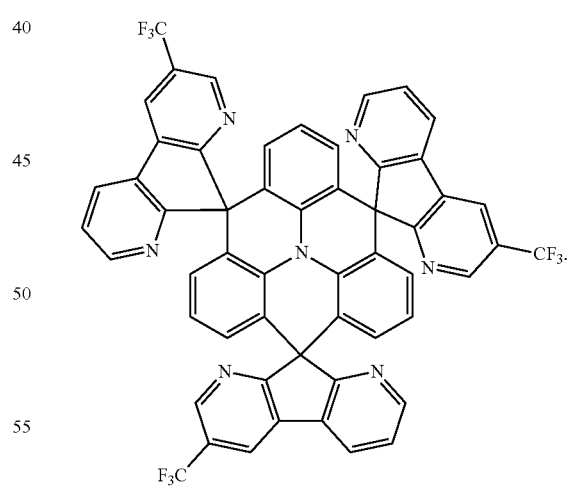
* * * * *